US007910553B2

(12) United States Patent
Mitra et al.

(10) Patent No.: US 7,910,553 B2
(45) Date of Patent: Mar. 22, 2011

(54) PEPTIDYL PRODRUGS THAT RESIST P-GLYCOPROTEIN MEDIATED DRUG EFFLUX

(75) Inventors: Ashim K. Mitra, Overland Park, KS (US); Soumyajit Majumdar, Oxford, MS (US); Ritesh Jain, Kansas City, MO (US); Yasser Nashed, Thousand Oaks, CA (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 11/677,947

(22) Filed: Feb. 22, 2007

(65) Prior Publication Data
US 2007/0142302 A1 Jun. 21, 2007

Related U.S. Application Data

(62) Division of application No. 11/285,754, filed on Nov. 22, 2005, now Pat. No. 7,214,664.

(60) Provisional application No. 60/633,366, filed on Dec. 3, 2004.

(51) Int. Cl.
*C07K 5/06* (2006.01)

(52) U.S. Cl. .......................................... 514/19; 530/331

(58) Field of Classification Search .................. 514/18, 514/19; 530/331
See application file for complete search history.

(56) References Cited

U.S. PATENT DOCUMENTS

| 5,405,850 | A | 4/1995 | Blumenkopf |
| 7,214,663 | B2 * | 5/2007 | Bebbington et al. ............ 514/18 |
| 7,214,664 | B2 | 5/2007 | Mitra et al. |
| 7,553,812 | B2 | 6/2009 | Mitra |
| 2005/0043246 | A1 | 2/2005 | Mitra |
| 2006/0135438 | A1 | 6/2006 | Mitra et al. |
| 2009/0082566 | A1 | 3/2009 | Mitra |
| 2009/0149482 | A1 | 6/2009 | Mitra et al. |

FOREIGN PATENT DOCUMENTS

WO   WO 03/048190   6/2003

OTHER PUBLICATIONS

"U.S. Appl. No. 12/194,248 ,Non-Final Office Action mailed Oct. 5, 2009", 8 Pgs.
"U.S. Appl. No. 10/854,533, Final Office Action mailed Nov. 1, 2007", 8 pgs.
"U.S. Appl. No. 10/854,533, Non-Final Office Action mailed Sep. 8, 2006", 6 pgs.
"U.S. Appl. No. 10/854,533, Response filed Dec. 1, 2006 to Non-Final Office Action mailed Sep. 8, 2006", 9 pgs.
"U.S. Appl. No. 10/854,533, Response filed Mar. 28, 2007 to Restriction Requirement mailed Feb. 26, 2007", 8 pgs.
"U.S. Appl. No. 10/854,533, Response filed Jun. 27, 2007 to Non-Final Office Action mailed Feb. 26, 2007", 8 pgs.
"U.S. Appl. No. 10/854,533, Response filed Jun. 30, 2006 to Restriction Requirement mailed May 16, 2006", 2 pgs.
"U.S. Appl. No. 10/854,533, Restriction Requirement mailed Feb. 26, 2007", 7 pgs.
"U.S. Appl. No. 10/854,533, Restriction Requirement mailed May 16, 2006", 9 pgs.
"U.S. Appl. No. 11/285,754, Non-Final Office Action mailed Jul. 25, 2006", 8 pgs.
"U.S. Appl. No. 11/285,754, Notice of Allowance mailed Dec. 26, 2006", 5 pgs.
"U.S. Appl. No. 11/285,754, Preliminary Amendment filed Feb. 8, 2006", 3 pgs.
"U.S. Appl. No. 11/285,754, Response filed Nov. 21, 2006 to Non-Final Office Action mailed Jul. 25, 2006", 10 pgs.
"U.S. Appl. No. 11/285,754, Response filed Jun. 20, 2006 to Restriction Requirement mailed May 26, 2006", 2 pgs.
"U.S. Appl. No. 11/285,754, Restriction Requirement mailed May 26, 2006", 7 pgs.
"International Application Serial No. PCT/US02/338846, International Preliminary Examination Report Dec. 20, 2004", 6 pgs.
"International Application Serial No. PCT/US02/338846, International Search Report Jul. 21, 2003", 5 pgs.
Colla, Leon , et al., "Synthesis and antiviral activity of water-soluble esters of acyclovir [9[(2-hydroxyethoxy)methyl]guanine]", *Journal of Medicinal Chemistry*, 26(4), (Apr. 1983),602-4.
Dey, Surajit , et al., "Molecular Evidence and Functional Expression of P-Glycoprotein (MDR1) in Human and Rabbit Cornea and Corneal Epithelial Ceil Lines", *Investigative Ophthalmology & Visual Science*, 44(7), (Jul. 2003),2909-2918.
Fricker, Gert , et al., "Modulation of Drug Transporters at the Blood-Brain Barrier", *Pharmacology*, 70(4), (2004),170-176.
Gao, Hongwu , et al., "Regioselective synthesis of various prodrugs of ganciclovir", *Tetrahedron Letters*, 41(8), (2000),1131-1136.
Gaucher, Berandere , "Prodrugs of HIV protease inhibitors-saquinavir, indinavir and nelfinavir-derived from diglycerides or amino acids: synthesis, stability and anti-HIV activity", *Org Biomol Chem.*, 2(3), (2004),345-57. Han, H. , "5'-Amino Acid Esters of Antiviral Nucleosides, Acyclovir, and AZT Are Absorbed by the Intestinal PEPT1 Peptide Transporter", *Pharmaceutical Research*, 15, (1998),1154-1159.
Irvine, Jennifer D., et al., "MDCK (Madin-Darby canine kidney) cells: A tool for membrane permeability screening", *Journal of Pharmaceutical Sciences*, 88(1), (Jan. 1999),28-33.
Jain, R. , et al., "Circumventing P-glycoprotein-mediated cellular efflux of quinidine by prodrug derivatization", *Molecular Pharmaceutics*, 1(4), (Jul.-Aug. 2004),290-299.
Jain, Ritesh , et al., "Evasion of P-gp mediated cellular efflux and permeability enhancement of HIV-protease inhibitor saquinavir by prodrug modification", *International Journal of Pharmaceutics*, 303(1-2), (2005),8-19.
Lee, Vincent H., "Membrane transporters", *European Journal of Pharmaceutical Sciences*, 11(Suppl 2), (Oct. 2000),S41-50.
Rouquayrol, Marielle , et al., "Transepithelial transport of prodrugs of the HIV protease inhibitors saquinavir, indinavir, and nelfinavir across Caco-2 cell monolayers", *Pharmacuetical Research*, 19(11), (Nov. 2002),1704-1712.
Vierling, Pierre , et al., "Prodrugs of HIV Protease Inhibitors", *Current Pharmaceutical Design*, 9(22), (2003),1755-1770.
"U.S. Appl. No. 10/854,533 response to Final Office Action mailed Nov. 1, 2007.", 19 pgs.
"U.S. Appl. No. 10/854,533 Notice of Allowance mailed Jul. 3, 2008.", 11 pgs.

* cited by examiner

*Primary Examiner* — David Lukton

(74) *Attorney, Agent, or Firm* — Stinson Morrison Hecker LLP

(57) ABSTRACT

A method of treating a patient for a condition wherein the bioactive agent of choice is DRUG, wherein DRUG is a substrate that is effluxed by the P-gp transporter, is provided, the method comprising administering to the patient an effective amount of a compound of formula (I):

DRUG-X—Y$_{(n)}$—Z$_{(n')}$—Z'$_{(n'')}$—R    (I)

wherein each X, Y, Z, and Z' is independently Met, Val, Thr, Tyr, Trp, Ser, Ala, or Gly; R is H or an amino-protecting group; n is 1, and each n', or n" is independently 0 or 1; or a pharmaceutically acceptable salt thereof, with the proviso that DRUG is not acyclovir or ganciclovir and that DRUG is non-peptidyl.

20 Claims, 9 Drawing Sheets

PEPTIDYL PRODRUGS THAT RESIST P-GLYCOPROTEIN MEDIATED DRUG EFFLUX

CROSS-REFERENCE TO RELATED APPLICATIONS

This application is a divisional application of U.S. patent application Ser. No. 11/285,754, filed Nov. 22, 2005, now U.S. Pat. No. 7,214,664, and claims the priority of U.S. provisional application Ser. No. 60/633,366, filed Dec. 3, 2004.

This invention was made with the support of the U.S. Government under National Institutes of Health Grant No. GM 64320-03. The Government has certain rights in the invention.

BACKGROUND OF THE INVENTION

P-Glycoprotein (P-gp) is a member of the large ATP binding cassette super family of transport proteins also called traffic ATPases. P-gp is composed of two homologous halves, each containing six transmembrane domains, separated by flexible linker polypeptides. P-gp is a 170 kDa membrane bound protein that effluxes a wide variety of structurally unrelated drugs out of cells. This efflux pump is responsible for export of wide variety of hydrophobic natural products, drugs, and linear and cyclic peptides from the cytoplasm and cytoplasmic membrane of eukaryotic cells, using energy from ATP hydrolysis.

Various mechanisms have been proposed to explain the efflux of drugs and various xenobiotics by this transporter. However, there are three prevalent models, the hydrophobic vacuum model (HVC), the pore model, and the flippase model that have been used to explain the mechanism by which P-gp effluxes out drugs. The hydrophobic vacuum model is the most widely accepted model of P-gp action. According to the HVC model P-gp acts as a vacuum cleaner, moving compounds that are substrates from the lipid bilayer into the extra cellular space.

P-gp is ubiquitously expressed on human tissues such as intestinal mucosa, brain capillary endothelial cells, biliary canaliculus, and kidney tubules. Thus, the ubiquitous presence of this transporter and the broad substrate specificity of P-gp makes it a major factor responsible for sub-therapeutic levels of various drugs in the blood and various tissues. Recently, it has been reported that presence of this transporter on the brush border membrane of the intestinal epithelium not only decreases the permeability of various bioactive agents but also increases the metabolism of various drugs by back effluxing the drugs and increasing the exposure time of the drug in the cells as well as in the lumen.

Thus, bioavailability of various anticancer drugs, anti-HIV drugs, calcium channel drugs, and other drugs which are P-gp substrates is limited by this efflux transporter. Over expression of P-gp by tumor cells confers multidrug resistance. Efflux of many anticancer drugs including taxol, vincristine, vinblastine, actinomycin D, colchicines, and daunorubicin, from tumor cells makes P-gp a major barrier to chemotherapy. High expression of this transporter on the blood-brain-barrier (BBB) restricts the entry into the brain of P-gp substrates such as anti-HIV drugs such as ritonavir, saquinavir, nelfinavir, and various anticancer drugs, and thus imposes a major challenge in the treatment of various diseases of the brain.

Expression of this efflux transporter on various body tissues and cells not only influences the in vivo disposition of various therapeutically active drugs but also greatly influences pharmacokinetics of the drug. It has been known that inhibition of P-gp by various modulators can lead to improved bioavailability of drugs across the intestines, the kidneys, and the BBB. Various modulators that are inhibitors of P-gp are often co-administered so that they can inhibit P-gp and increase bioavailability when given simultaneously with other bioactive agents. However, usage of these compounds is limited by their toxicity, owing to the high serum concentration that is achieved with the doses required to inhibit P-gp. Thus, although various approaches have been studied to overcome P-gp mediated drug efflux, P-gp remains a major barrier to bioavailability, chemotherapy, and effective permeation of P-gp substrates into the brain and other tissues.

Besides efflux transporters, such as P-gp, there are various membrane transporters/receptors, such as peptide or vitamin transporters, that help in the influx of various nutrients and other compounds that are substrates for these transporters into various organs, cells, and across various barriers, including the blood brain barrier.

Thus, there exists a need for bioactive compounds that are not recognized by P-gp as a substrate, but that are substrates of membrane transporters/receptors. There is also a need for increasing the bioavailability of bioactive compounds that are P-gp substrates. Further, there is a need to increase the concentration of bioactive compounds that are P-gp substrates in sanctuary sites of a mammalian subject. Still further, there is a need to enhance delivery to cells of bioactive compounds that are P-gp substrates.

SUMMARY OF THE INVENTION

The present invention provides compounds of formula (I) that are amino acid ester derivatives of bioactive compounds, and di-, tri, and tetra-peptide ester derivatives of bioactive compounds, wherein the bioactive compounds are P-gp substrates, and the derivatives are not recognized by P-gp as a substrate:

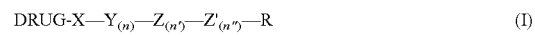

$$\text{DRUG-X}-Y_{(n)}-Z_{(n')}-Z'_{(n'')}-R \qquad (I)$$

wherein DRUG represents a bioactive compound, such as a therapeutic agent; each X, Y, Z, and Z' is independently Met, Val, Thr, Tyr, Trp, Ser, Ala, or Gly; R is H or an amino-protecting group; n is 1, and each n' or n" is independently 0 or 1, or pharmaceutically acceptable salts thereof.

The invention also provides a pharmaceutical composition comprising a compound of the invention and pharmaceutically acceptable carrier.

The present invention also provides the use of a compound of the invention in medical therapy.

Some of the compounds of formula (I) are useful as intermediates for the preparation of other compounds of formula (I), as shown below. Novel methods and intermediates used to prepare a compound of the invention are also within the scope of the invention.

The present invention provides a method of converting drugs that are substrates for the P-gp transporter into derivatives that are not recognized by P-gp as a substrate, and/or that are preferably targeted to and recognized by an influx membrane transporter/receptor, such as a peptide, vitamin or other nutrient transporter. The efflux of such derivatives from cells by the P-gp transporter is thus eliminated or substantially reduced, while their transport into target cells by one or more influx transporters/receptors can be effectively enhanced.

The present invention further provides treating a patient for a condition wherein the bioactive, e.g., therapeutic agent of choice is a substrate that is effluxed by the P-gp transporter, comprising administering to the patient an effective amount of a compound of formula (I).

The present invention further provides a method for enhancing delivery to a cell, e.g., a mammalian cell, of a bioactive, e.g., therapeutic agent that is a substrate that is effluxed by the P-gp transporter comprising linking the agent to one or more (e.g., 1, 2, 3, or 4) groups of the formula —X—Y$_{(n)}$—Z$_{(n')}$—Z'$_{(n'')}$—R; wherein each X, Y, Z, and Z' is independently Met, Val, Thr, Tyr, Trp, Ser, Ala, or Gly; R is independently H or an amino-protecting group; and each n' or n'' is independently 0 or 1; and administering the resulting compound to the cell.

The present invention still further provides a method of improving the bioavailability in a mammalian patient of a bioactive agent that is a substrate that is effluxed by the P-gp transporter and/or imported by a nutrient transporter/receptor which comprises administering to the patient an effective amount of the compound of formula (I).

The present invention still further provides a method of increasing the concentration of a bioactive agent in sanctuary sites of a mammalian patient which comprises administering to the patient an effective amount of the compound of formula (I).

One embodiment of the present invention provides a bioactive agent linked to one or more (e.g., 1, 2, 3, or 4) groups of the formula —X—Y$_{(n)}$—Z$_{(n')}$—Z'$_{(n'')}$—R; wherein each X, Y, Z, and Z' is independently Met, Val, Thr, Tyr, Trp, Ser, Ala or Gly; R is H or an amino-protecting group; n is 1, and each n' or n'' is independently 0 or 1.

Without wishing to be bound by theory, it is believed that the peptide portions of compounds of the invention target and bind to nutrient transporters/receptors and thereby assist and enhance cellular internalization of the compounds of the invention. It is believed also that the compounds of the invention may function as prodrugs, being hydrolyzed intracellularly and releasing the free bioactive agent, which under this theory would be responsible for the biological activity of the compounds.

Advantageously, with the compounds of the present invention, microsomal metabolism of the free bioactive agent (DRUG) is reduced, protein binding is reduced when a polar peptide is used in the derivatization, and the compounds are more soluble than the free DRUGS if polar/ionic molecules are used in the derivatization.

DETAILED DESCRIPTION OF THE INVENTION

Figure 1:
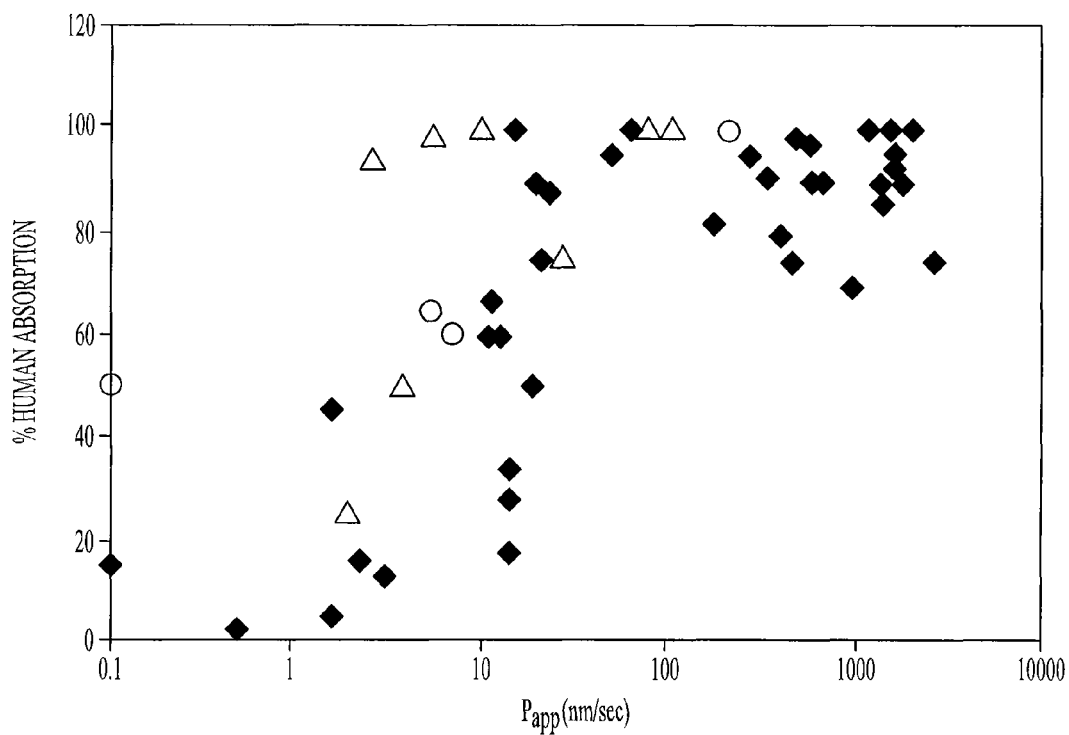
FIG. 1 is a plot showing the relationship between apparent permeability (Papp) values in the MDCK cell line and percent (%) human intestinal absorption. The Papp values plotted at 0.1 are actually ≦0.1, including zero for compounds not detected in the basolateral compartment. The symbol (♦) represents passive diffusion compounds; the symbol (Δ) represents active transport compounds; and the symbol (○) represents efflux substrates (*J. Pharm. Sci.* 1999, 88, 28-33).

The following definitions are used, unless otherwise described:

The terms "nutrient transporter" and "membrane nutrient transporter" mean various membrane transporters/receptors such as peptide or vitamin transporters/receptors, that help in the influx of various nutrients and other compounds that are substrates for these transporters into various organs, cells, and across various biological barriers, such as the blood brain barrier. The term does not include efflux transporters, such as P-gp.

The term "amino acid," comprises particular natural amino acids (e.g., Ala, Arg, Asn, Asp, Cys, Glu, Gln, Gly, His, Hyl, Hyp, Ile, Leu, Lys, Met, Phe, Pro, Ser, Thr, Trp, Tyr, and Val), and includes the derivatives (e.g., Sar) and residues of the natural amino acids. The terms "amino acid" and particular amino acids (e.g., Met, Val, Thr, Tyr, Trp, Ser, Ala, or Gly) include amino acid residues and include both the D and L stereoisomeric forms.

The abbreviation Q refers to quinidine.

The abbreviation SAQ refers to saquinavir.

The term "individual" or "patient" refers to any animal, including mammals, preferably mice, rats, other rodents, rabbits, dogs, cats, swine, cattle, sheep, horses, or primates, and most preferably humans. The term may specify male or female or both, or exclude male or female.

The term "treatment" or "treating" means administration of a compound for purposes including:

(i) preventing the disease or condition, that is, causing the clinical symptoms of the disease or condition not to develop;

(ii) inhibiting the disease or condition, that is, arresting the development of clinical symptoms; and/or (iii) relieving the disease or condition, that is, causing the regression of clinical symptoms.

The term "effective amount" means a dosage sufficient to provide treatment for the disease state or condition being treated. This will vary depending on the patient, the disease, and the treatment being effected.

The term "bioactive agent" includes any compound that causes a desirable change in the activity of cells, tissues, or organs when it is desired to be delivered to target cells, tissues, or organs. In accordance with the present invention, bioactive agents include, but are not limited to, nutrients, conventional therapeutic agents, and radioisotopes.

The term "non-peptidyl" means that the drug is not a bioactive poly- or oligo-peptide, e.g., is not made up entirely of α-amino acid residues.

Accordingly, the invention provides a compound of formula (I):

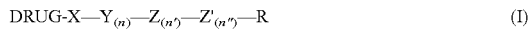

DRUG-X—Y$_{(n)}$—Z$_{(n')}$—Z'$_{(n'')}$—R  (I)

wherein DRUG is a bioactive agent that is a P-glycoprotein substrate; each X, Y, Z, and Z' is independently Met, Val, Thr, Tyr, Trp, Ser, Ala, or Gly; R is independently H or an amino-protecting group; n is 1, and each n' or n" is independently 0 or 1; or a pharmaceutically acceptable salt thereof, with the proviso that DRUG is not acyclovir or ganciclovir. Preferably, DRUG is not a bioactive nucleoside, terpenoid, or peptide.

In a particular embodiment of the compounds of the invention, each Y and X is individually Gly or Val.

In a particular embodiment of the compounds of the invention, R is H, acetyl, or t-butoxycarbonyl.

In a particular embodiment of the compounds of the invention, each R is H.

Table I below lists bioactive agents that are substrates that are effluxed by the P-gp transporter and thus are suitable for derivatization according to the present invention.

TABLE I

Antiarrhythmics Drugs-amiodarone, lidocaine, quinidine
Antimalarials and antiparasites-chloroquine, emetine, hydroxychloroquine, quinacrine, quinine
Antibiotics and antifungals-cefoperazone, ceftriazone, erythromycin, itraconazole, ketoconazole, aureobasidin A
Calcium channel blockers-bepridil, diltiazem, felodipine, nifedipine, nisoldipine, nitrendipine, tiapamil, verapamil
Calmodulin antagonist-chlorpromazine, trifluperazine
Cancer chemotherapeutics-actinomycin D, colchicines, daunorubicin, doxorubicin, etoposide, mitomycin C, mithramycin, podophyllotoxin, puromycin, taxol, topotecan, triamterene, vinblastine, vincristine
See U.S. Pat. No. 6,767,531.
Fluorescent dyes-BCECF-AM, Fluro-2, Fura-2, Rhodamine 123, Hoechst 33342
HIV protease inhibitors-indinavir, nelfinavir, ritonavir, saquinavir
Hormones-aldosterone, clomiphene, cortisol, deoxycorticosterone, dexamethosone, prednisone, progesterone analogs, tamoxifen, hydrocortisone, testosterone
Immunosuppressants-cyclosporine A, cyclosporine H, tacrolimus, sirolimus
Indole alkaloids-reserpine, yohimbine
Local anaesthetics-bupivacaine
See U.S. Pat. No. 5,510,339.
Surfactants/solvents-cremophor-EL, triton X-100, Tween 80
Toxic peptides-N-Acetyl-leucyl-leucinal, gramicidine D, valinomycin
Tricyclic antidepressants desipramine, trazodone
Miscellaneous-components of grape and citrus fruit juice, ethidium bromide, ivermectin, liposomes, quercetin, valspodar, terfenadine, tumor necrosis factor, Vitamin A All of these classes of bioactive agents can be derivatized with amino acids (e.g., valine) or oligopeptides at one or more attachment sites that yield, for example, ester or amido linkages. In addition, attachment methods to hydroxyalkyl groups that yield acyclovir derivatives are disclosed in U.S. patent application Ser. No. 10/854,533, filed May 26, 2004, which is incorporated by reference herein.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art. For example, salts of the enol form of the compound of formula (I) may be prepared in the usual manner by reacting the keto form with one or more equivalents of a desired base such as, for example, a metallic hydroxide base, e.g., sodium hydroxide; a metal carbonate or bicarbonate base such as, for example, sodium carbonate or sodium bicarbonate.

Acid addition salts of the present compounds may be prepared by reacting the present compounds with one or more equivalents of the desired inorganic or organic acid, such as, for example, hydrochloric acid. Esters, ketals, and acetals of hydroxyl groups of the compounds may also be prepared by any of the usual methods known in the art for esterifying or protecting OH groups.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

Processes for preparing compounds of formula I are provided as further embodiments of the invention and are illustrated by the procedures described in the examples. Specifically, the compounds of formula (I) can be prepared from convenient starting materials, employing procedures (e.g., reagents and reaction conditions) known to those of skill in the art. For example, suitable reagents and reaction conditions are disclosed, e.g, in *Advanced Organic Chemistry, Part B: Reactions and Synthesis*, Second Edition, Cary and Sundberg (1983); *Advanced Organic Chemistry, Reactions, Mechanisms, and Structure*, Second Edition, March (1977).

The compounds of the invention may be prepared by attaching an amino acid residue or an oligopeptide, such as a di-, tri- or tetrapeptide, to a bioactive agent that is a substrate for the P-gp transporter, so as to convert the bioactive agent effectively into a substrate for a nutrient transporter, while retaining an effective amount of the bioactive agent's bioactivity at the target sites. Useful amino acid and di-peptidyl derivatives include Val-Val-Val-, Val-Gly, Gly-Val, Gly-Gly-, Tyr-Val-, Val-Tyr-, and combinations of peptidyl residues with similar polarity, up to about, e.g., 5-10 residues. These peptides are readily attached to functional groups on DRUG such as hydroxy, thiol, acryl, epoxy, carboxy, amino and the like. In situ, the compounds of the invention are converted to the parent drug by intracellular cholinesterases, aminopeptidases, and dipeptidases, that cleave the amino acid and oligopeptide residues from the active moiety.

Amino-protecting groups, R, are available to the art of polypeptide synthesis, and include ($C_2$-$C_4$)acyl, i.e., acetyl, benzyl, carbobenzyloxy (CBZ), t-butylcarbobenzoxyl (t-Boc), benzoyl, and the like. *Protecting Groups in Organic Synthesis*, Second Edition, Greene, T. W., and Wutz, P. G. M., John Wiley & Sons, New York; and *Comprehensive Organic Transformations*, Larock, R. C., Second Edition, John Wiley & Sons, New York (1999). N-acyl derivatives of amino groups of the present peptide moieties may be prepared by utilizing an N-acyl protected amino acid for the final condensation, or by acylating a protected or unprotected peptide. O-acyl derivatives may be prepared, for example, by acylation of a free hydroxy peptide. Either acylation may be carried out using standard acylating reagents such as acyl halides, anhydrides, acyl imidazoles, and the like. Both N- and O-acylation may be carried out together, if desired.

Methods to test compounds of the invention for desired properties or biological activity are known to persons of skill in the art. For instance, methods to test for uptake into target cells, such as the cornea of the eye, are provided in the examples below.

The compounds of formula I of the instant invention may be formulated into pharmaceutical compositions in a variety of forms and administered to target cells or to a human host, such as a human patient, in need of treatment. Once the compound crosses the cellular membrane, the amino acid or peptidyl moiety is cleaved via a biotransformation, producing the free drug. Dosages can readily be determined based on the quantity, e.g., molar quantity, of free agent ("DRUG") that is released from the compound, assuming a complete biotransformation of the compound. The desired quantity of free agent is in turn the effective dosage administered to the patient undergoing treatment for a particular condition. Preferably, patients or target cells that efflux DRUG are identified before being treated. Additionally or alternatively, before treatment the DRUG is preferably pre-identified as a bioactive agent that will be effluxed by the patient or by the target cells. Methods for the extrapolation of effective dosages in mice and other animals to humans are known in the art; for example see U.S. Pat. No. 4,938,949.

The pharmaceutically and physiologically acceptable compositions may be administered by any number of routes including, but not limited to, parenteral, subcutaneous, intracranial, intraocular, intracapsular, intraspinal, intracisternal, intrapulmonary (inhaled), oral, intravenous, intramuscular, intra-arterial, intramedullary, intrathecal, intraventricular, transdermal, subcutaneous, intraperitoneal, intranasal, enteral, topical, sublingual, or rectal means.

Thus, the present compounds may be administered systemically, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. The amount of active compound in such therapeutically useful compositions is such that an effective dosage level of the free drug will be obtained.

The tablets, troches, pills, capsules, and the like may also contain the following: binders such as gum tragacanth, acacia, corn starch or gelatin; excipients such as dicalcium phosphate, povidone, or croscarmellose sodium; a disintegrating agent such as corn starch, potato starch, alginic acid, sodium starch glycolate, and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar, and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders, for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. They may also be administered to the skin as compositions or formulations, in combination with a dermatologically acceptable carrier, which may be a solid or a liquid.

Useful solid carriers include finely divided solids such as talc, clay, microcrystalline cellulose, silica, alumina, and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820, 508).

The present compounds can also be delivered from controlled release intraocular devices such as contact lens-type inserts, other ocular inserts, and polymeric patches and bandages. Useful dosages of the compounds of the invention can be determined by comparing their in vitro activity, and in vivo activity in animal models. Methods for the extrapolation of effective dosages in mice, and other animals, to humans are known to the art; for example, see U.S. Pat. No. 4,938,949.

This invention relates to the discovery that certain derivatives of P-gp substrates circumvent the P-gp efflux transporter, while preferably exhibiting enhanced affinity for nutrient transporters. This results in higher bioavailability of the free drug at targeted sites as well as higher bioavailability in sanctuary sites, such as the brain, spinal cord, intestines, kidneys, bone-marrow, and lungs.

Thus, in a preferred embodiment, the instant invention is useful in drug treatment with various anticancer drugs, anti HIV drugs (such as HIV protease inhibitors), calcium channel drugs, and other drugs that are P-gp substrates and have limited bioavailability attributable to this efflux transporter. In another preferred embodiment, the instant invention is useful in drug treatment of viral diseases wherein the virus persists in sanctuary sites.

The use of HIV protease inhibitors (PIs) has substantially improved the clinical outcome for HIV-infected individuals. However, complete eradication of HIV infection is still an elusive goal. Sub-therapeutic concentrations of PIs in sanctuary sites like the brain, lung, and bone-marrow cause persistence of viral infections, and may lead to drug resistance. One of the factors that may limit the therapeutic efficacy of PIs is the cellular efflux caused by proteins like P-gp, multidrug resistance associated proteins (MRPs), and breast cancer resistance protein (BCRP), which are present on various biological barriers, such as enterocytes, brain vascular endothelial cells, and alveolar epithelia. Modification of PIs according to the present invention bypasses the efflux proteins and results in greater availability of the free drug in the sanctuary sites.

The derivatives of P-gp substrates, according to the present invention, preferably target membrane nutrient transporters. When a substrate binds to a nutrient transporter it triggers a conformational change in the transport protein as a result of which it translocates across the membrane into the cytoplasm of the cell. During this process the substrate is not freely available in the inner leaflet of the cell membrane and may avoid efflux by P-gp. Suitable membrane nutrient transporters include, but are not limited to, amino acid transporters, peptide transporters, monocarboxylate transporters, organic anion transporters, and organic cationic transporters. Such targeting will lead to the by-passing of P-gp mediated efflux, and to higher concentrations of the bioactive agent at the target site.

It is believed that when a P-gp substrate is modified by derivatization with an amino acid residue or an oligopeptide so that is translocated by a membrane transporter, the P-gp substrate is not available in the membrane leaflet for P-gp to vacuum-up and efflux. This in turn leads to higher bioavailability of the free drug at the target sites.

The cumulative effects of poor aqueous solubility, efflux transporters, metabolizing enzymes, and plasma protein binding are responsible for low bioavailability (V. J. Wacher et al., *J. Pharm. Sci.* 1998, 87, 1322-30 and P. B. Watkins, *Adv. Drug Deliv. Rev.* 1997, 27, 161-170). Advantageously, with the compounds of the present invention, microsomal metabolism of the free drug is reduced, protein binding is reduced when a polar peptide is used in the derivatization, and the compound is more water soluble than the free drug if polar/ionic molecules are used in the derivatization.

For example, in accord with the invention, quinidine, a known substrate for P-gp, was modified by attaching the amino acid valine (val), to yield valquinidine, and by attaching the dipeptide valine-valine (val-val) to yield valvalquinidine. The uptake studies in Example 5 using the MDCKII-MDR1 cell line demonstrate that valquinidine and valvalquinidine do not show any significant effect on [$^3$H] ritonavir uptake, a well-known P-gp substrate. However, when an equimolar quantity of quinidine is used, there is a marked increase in [$^3$H] ritonavir uptake by the MDCKII-MDR1 cells. The results confirm that quinidine is a P-gp substrate whereas valquinidine and valvalquinidine are not P-gp substrates. Example 5 below establishes not only that valquinidine and valvalquinidine are not substrates for the P-gp efflux transporter, but also that they are substrates of peptide and amino acid transporters.

The results from this experiment indicate that transporter targeted derivatization of P-gp substrates can by-pass P-gp mediated efflux. This approach can help overcome P-gp mediated drug resistance of tumor cells as well as enhance permeation of P-gp substrates across the BBB and the intestinal epithelium.

Saquinavir (SAQ), an HIV protease inhibitor and another known substrate for P-gp, was modified by attaching the amino acid valine (val) to give Val-SAQ, by attaching the dipeptide valine-valine (val-val) to give Val-Val-SAQ, and by attaching the dipeptide glycine-valine (gly-val) to give Gly-Val-SAQ. Example 6 below establishes that this modification of SAQ results in a decreased affinity of the molecule for the efflux transporter. As shown in Example 8, the decrease in secretory transport and the increase in absorptive transport of SAQ derivatives according to the present invention as compared to saquinavir can lead to increased absorption of these derivatives across various biological membranes.

Figure 2:
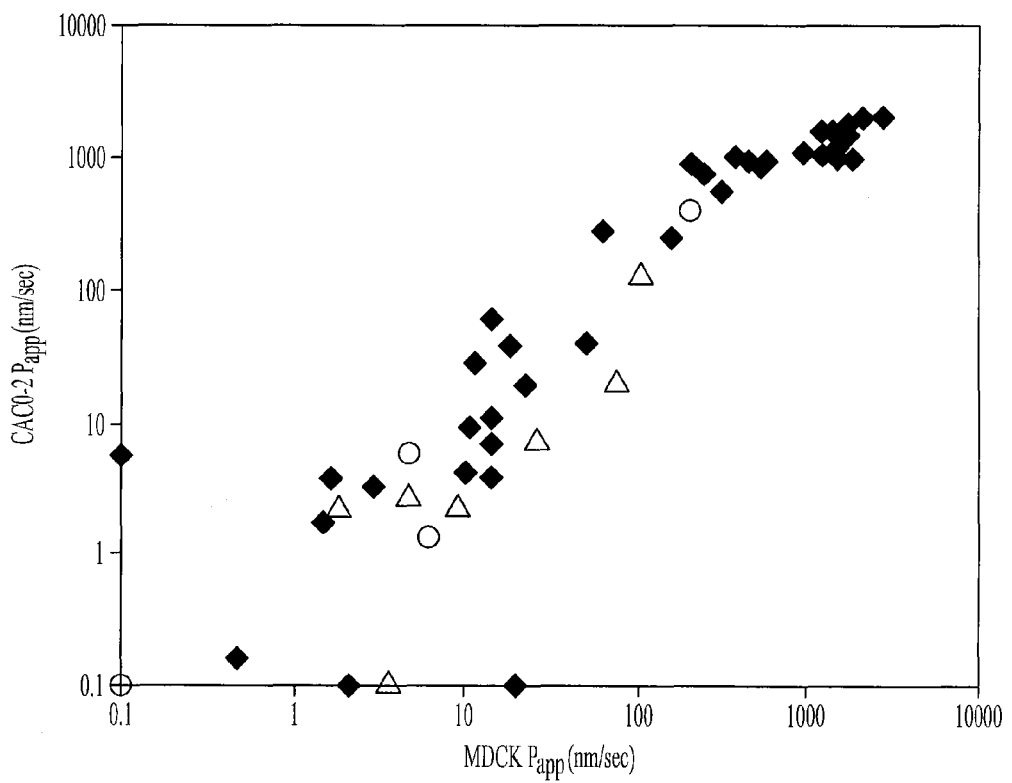
FIG. 2 shows a plot of the correlation of MDCK and Caco-2 apparent permeability (Papp) values. Papp values plotted at 0.1 are actually ≦0.1, including zero for compounds not detected in the basolateral compartment. The symbol (♦) represents passive diffusion compounds; the symbol (Δ) represents active transport compounds; and the symbol (○) represents efflux substrates (*J. Pharm. Sci.* 1999, 88, 28-33).

Example 5 shows that P-gp did not recognize valquinidine or valvalquinidine as substrates. Uptake studies were conducted using Madin-Darby canine kidney (MDCK) cells, a dog renal epithelial cell line. MDCKII-MDR1 cells are MDCK cells transfected with the MDR gene. The cells express high levels of P-gp. In these studies a transfected MDCKII-MDR1 cell line was used as a screening model, as this system has the advantages of rapid growth as well as high levels of P-gp expression. The MDCKII-MDR1 cell line grows much faster than Caco-2 cells, a well-known model for mechanistic studies of drug absorption that is also used in screening assays for preclinical drug selection. Apparent permeability (Papp) values obtained from Caco-2 transport studies have been shown to correlate to human intestinal absorption (P. Artursson et al., *Bioichim. Biophys. Res. Comm.* 1991, 175, 80-885 and B. H. Stewart et al., *Pharm. Res.* 1995, 12, 693-699). Furthermore, apparent permeability (Papp) values of MDCK and Caco-2 cells correlate well with each other (FIG. 2). These results indicate that MDCK cells are a useful tool for rapid membrane permeability screening vis-a-vis intestinal and other epithelial barriers.

Many in vitro models have been used to study intestinal permeability in order to predict oral absorption in humans. An in vitro-in vivo correlation attempts to link in vitro drug product performance to in vivo biopharmaceutical-pharmacokinetic performance. For orally administered drugs, dissolution and intestinal permeation have long been recognized as two possible rate-limiting phenomena in absorption processes. Oral absorption involves the permeation of drug molecules across the intestinal epithelium as well as metabolism on the cell surface or in the enterocyte itself. Permeability directly measures the interaction between drug molecules and cells. Prediction of oral bioavailability in humans can be based on a correlation between permeability measurements of a series of molecules across MDCKII-MDR1 with drug absorption in humans (FIG. 1). In addition, the permeability data from MDCK have been found independently to correlate well with human bioavailability (J. D. Irvine, et al., *J. Pharm. Sci.* 1999, 88, 28-33). Therefore, the results with the MDCKII-MDR1 cell line appear to be a predictive model for efficacy of the compounds of the present invention in the treatment of humans.

In addition, intact rabbit corneas can be a predictive in vivo model for ocular drug delivery and bioavailability in humans. Molecular identification and functional characterization of P-gp has been reported in human and rabbit corneas and in rabbit corneal cell lines (S. Dey et al., *Invest. Opth. Vis. Sci.* 2003, 44, 2909-18). It has also been proven that P-gp restricts ocular drug absorption, resulting in low ocular bioavailability (S. Dey et al., *J. Pharm. Exp. Ther.* 2004, 311, 246-55). Functional evidence of an oligopeptide transport system present on the rabbit cornea has also been established. The peptide transporter on the corneal epithelium may be targeted to improve the ocular bioavailability of poorly absorbed drugs (B. Anand et al., *Pharm. Res.* 2002, 19, 1194-202).

Example 11 shows that P-gp also has been found to be active in vivo. P-gp restricts topical absorption of erythromycin across rabbit corneas, but the bioavailability of P-gp substrates can be enhanced significantly by proper selection of P-gp inhibitors or by converting the substrates into the compounds of the present invention (S. Dey et al., *J. Pharm. Exp. Ther.* 2004, 311, 246-55).

The invention will now be illustrated by the following non-limiting examples. The following abbreviations are used in the examples:

Boc: t-butoxycarbonyl
DCC: dicyclohexylcarbodiimide
DMAP: 4-(N,N-dimethylamino)pyridine
DMEM: Dulbecco's modified Eagle's Medium
DMF: dimethylformamide
DPBS: Dulbecco's phosphate-buffered saline
IPBS: Isotonic phosphate buffer solution
MEM: Minimum Essential Medium
TFA: trifluoroacetic acid
TEA: triethyl amine All research was conducted strictly according to the principles embodied in the declaration of Helsinki and The Guiding Principles in the Care and Use of Animals (DHEW Publication NIH 80-23). All studies involving rabbis were conducted according to the Association for Research in Vision and Ophthalmology (ARVO) Statement for the Use of Animals in Ophthalmic and Vision Research.

EXAMPLE 1

Synthesis of Val-Quinidine

Boc-Val-OH (2.00 g., 9.26 mmol) and DCC (1.90 g, 9.26 mmol) were dissolved in dry DMF (20 ml) under a nitrogen atmosphere. The mixture was stirred continuously for one hour at 0° C. A solution of quinidine (1.50 g, 4.63 mmol) and DMAP (0.06 g, -0.65 mmol) in DMF (100 ml) was added dropwise to the reaction mixture at 0° C. The reaction mixture was stirred and allowed to warm to room temperature. After 24 hours, the reaction was checked by TLC (1:13 methanol/dichloromethane mixture) and LC-MS analysis, and was found to be complete. The urea derivative was removed by filtration and washed with ethyl acetate. Solvents from the combined filtrate and washing were totally removed under reduced pressure.

The resulting oil was dissolved in ethyl acetate and washed three times with a 5% $NaHCO_3$ solution. Each time, the organic layer was separated and the combined layers were dried over anhydrous magnesium sulfate. Ethyl acetate was rotary evaporated at 40° C., and the oily residue was redissolved in ethyl acetate and kept at 4° C. for 3 hours. The white precipitate was removed by filtration and washed with another small amount of ethyl acetate. The solvent was removed with a rotary evaporator at 40° C., and the compound was completely dried under vacuum (92% yield). The product Boc-Val-Q was confirmed by LC-MS analysis.

Boc-Val-Q (3.00 g) was dissolved in TFA (60 ml) and stirred at 0° C. for one hour. The excess acid was removed under vacuum, and the oily residue was mixed with toluene (100 ml) and rotary evaporated at 40° C. The product Val-Q was kept under vacuum overnight until it was completely dry.

Val-Q was a highly hygroscopic yellowish solid fluffy material (yield of 3.21 g). The structure was confirmed by $^1$H NMR and LC-MS analysis.

EXAMPLE 2

Synthesis of Amino Acid and Dipeptide Derivatives of Saquinavir

The general method to synthesize saquinavir derivatives according to the present invention is to conjugate the ligand with the hydroxyl group on saquinavir. The carboxylic group of the amino acid or peptide can form the ester link with saquinavir. Such modification may improve the delivery of saquinavir by targeting the amino acid transporter. Derivatives of other P-gp substrates bearing a hydroxyl group may be prepared analogously. In brief, the synthetic scheme includes i) formation the amino acid anhydrides, ii) coupling the anhydride with saquinavir, iii) removing the N-protection group, iv) neutralizing the conjugate, v) coupling the conjugate with an amino acid anhydride to form the peptide bond, and vi) removing the N-protection group. The overall procedure is shown in Scheme 1. Tri- and tetra-peptide analogs may be prepared analogously. The synthesis of Val-saquinavir 4 includes the first three steps with DCC as the coupling reagent. Boc-valine 2 and DCC are stirred for 1 hr in methylene chloride under a nitrogen atmosphere.

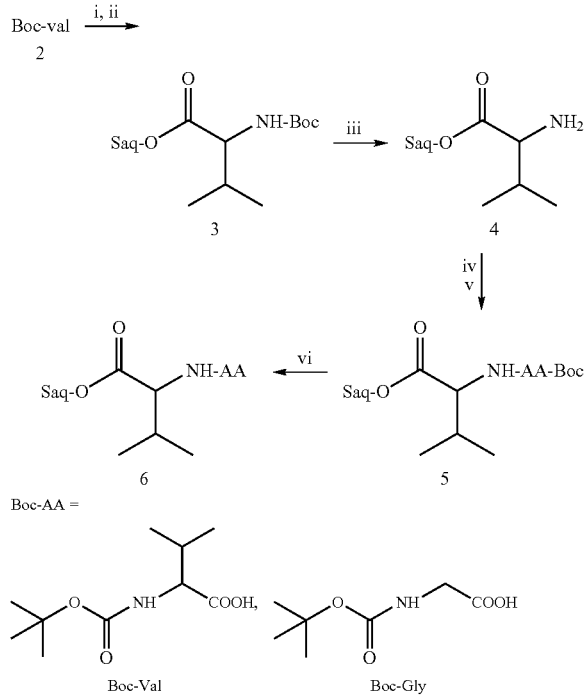

Scheme 1 i) DCC, CH$_2$Cl$_2$, 0° C., 1 h. ii) squinavir, DMAP, rt, 24 hrs. iii) TFA, 0° C., 1 h.
iv) TEA, 5 mins. v) Boc-AA, DCC, DMAP, CH$_2$Cl$_2$, rt, 24 hrs. vi) TFA, 0° C., 1 hr.

A. Synthesis of Val-SQV

Synthesis of Val-SQV involves the first three steps with dicyclohexylcarbodiimide (DCC) as the coupling reagent. Boc-valine 0.33 g (1.5 mmol) and 0.16 g (0.77 mmol) of DCC were stirred for 1 h in methylene chloride under nitrogen atmosphere (Scheme 1). Then, 0.5 g (0.75 mmol) of SQV and DMAP were added dropwise into the solution and was stirred continually for 24 h at room temperature. After filtration, the solvent was removed in vacuo and the residue was purified by column chromatography with methylene chloride:methanol (6:1) as eluant. The product, Boc-Val-SQV was treated with trifluoroacetic acid (TFA) for 1 h at 0° C. After removing TFA, the residue was co-evaporated with toluene, which generated the final product. Approximately, 0.61 g pure Val-SQV (TFA salt) is obtained as the white solid with yield of 95%. The purity of the prodrug is checked by TLC and LC-MS.

ESI-MS (M+1): 770.4; calculated (C$_{43}$H$_{59}$O$_6$N$_7$): 769.4 (5). $^1$H NMR of Val-SQV was $^1$H NMR (DMSO): δ 8.89 (1 H, d, H$^{11}$), 8.52 (1 H, m,H$^7$), 8.42 (4 H, bd, H$^{39}$, H$^3$), 8.21 (2 H, d, H$^{1,6}$), 8.08 (1 H, m, H$^4$), 7.86 (1 H, m, H$^2$), 7.74 (1 H, m, H$^2$), 7.63 (2 H, bd, H$^{15,17}$), 7.01-7.20 (5 H, m, H$^{21-25}$), 5.52 (1 H, m, H$^{26}$), 4.83 (1 H, m, H$^{12}$), 4.58 (1 H, m, H$^{18}$), 3.85 (1 H, m, H$^{4'}$), 3.26 (1 H, m, H$^{29}$), 2.3-2.74 (7 H, m, H$^{13,19,27,37}$), 1.59-1.99 (13 H, m, H$^{2'}$, H$^{30-36}$), 1.36 (9 H, s, H$^{41-43}$), 1.06 (6 H, dd, H$^{1'}$).

B. Synthesis of Val-Val-SQV and Gly-Val-SQV Prodrugs from Val-SQV

Val-SQV (TFA salt) 0.2 g (0.23 mmol) was treated with 0.8 mL TEA for 10 min. The mixture was added to the Boc-valine anhydride solution prepared according to the procedure described above. The reaction mixture was stirred overnight. After removing the precipitate (DCU) and most of the solvent, the residue was loaded onto the silica gel column and purified with CH$_2$Cl/MeOH. About 0.21 g of Val-Val-SQV (TFA salt) was obtained as a white solid with high purity (>95%) after removing the Boc group. By adding the Val-SQV into the Boc-glycine anhydride solution as described above, the Gly-Val-SQV (TFA salt) was synthesized (yield: 93%).

C. Gly-Val-saquinavir

ESI-MS (M+1): 827.4; calculated (C$_{45}$H$_{62}$O$_7$N$_8$): 826.4 (7). $^1$H NMR (DMSO): δ 8.78 (1 H, d, H$^{11}$), 8.60 (1 H, m, H$^7$), 8.1 (8 H, bd, H$^{1,4,6,39}$, H$^{1',3'}$), 7.86 (1 H, m, H$^2$), 7.73 (1 H, m, H$^3$), 7.52 (2 H, d, H$^{15,17}$), 7.0-7.21 (5 H, m, H$^{21-25}$), 5.38 (1 H, m, H$^{26}$), 4.81 (1 H, m, H$^{12}$), 4.42 (1 H, m, H$^{18}$), 3.75 (3 H, m, H$^{2',6'}$), 2.18-3.21 (9 H, m, H$^{13,19,27,29,37}$), 1.54-1.95 (13 H, m, H$^{30-36}$, H$^{5'}$), 1.32 (9 H, s, H$^{41-43}$), 0.92 (6 H, s, H$^{4'}$).

D. Val-Val-saquinavir

ESI-MS (M+1): 869.4; calculated (C$_{48}$H$_{68}$O$_7$N$_8$): 868.5 (2). $^1$H NMR (DMSO): δ 8.78 (1 H, d, H$^1$), 8.62 (1 H, m, H$^7$), 8.19 (2 H, d, H$^{1,6}$), 8.10 (6 H, bd, H$^{1,4,39}$, H$^{4',5'}$), 7.87 (1 H, m, H$^2$), 7.74 (1 H, m, H$^3$), 7.39 (2 H, bd, H$^{15,17}$), 6.95-7.05 (5 H, m, H$^{21-25}$), 5.24 (1 H, m, H$^{26}$), 4.83 (1 H, m, H$^{12}$), 3.77 (5 H, m, H$^{29}$, H$^{3',8'}$), 1.81-3.01 (21 H, m, H$^{13,19,27,30-37}$, H$^{2',7'}$), 1.28 (9 H, s, H$^{41}$), 0.94 (12 H, m, H$^{1',6'}$).

EXAMPLE 3

MDCKII-MDR1 Cell Culture

MDCK cells, retrovirally transfected with human MDR1 cDNA were obtained as a gift from Dr. Piet Borst (Netherlands Cancer Institute, Amsterdam). These MDCKII-MDR1 cells (passages 4-10) were cultured at 37° C. in a humidified atmosphere with 5% CO$_2$. Confluency was assessed by light microscopy. Cells were passaged at 70-80% confluence using 0.25% trypsin EDTA and were seeded at a density of 50,000 cells/cm$^2$ on 12-well tissue culture plates or on collagen coated Transwell® inserts and were maintained in DMEM, supplemented with 10% calf serum, 100 U/mL penicillin, 100 μg/mL streptomycin, 1% (v/v) non-essential amino acid, 3.7 g of sodium bicarbonate and 10 mM HEPES, pH 7.4. Cells were allowed to grow for 5-8 days. Integrity of monolayers formed on transwell was evaluated by monitoring [$^{14}$C]mannitol permeability and transepithelial electric resistance (TEER), with an epithelial volt ohmmeter (EVOM; World Precision Instruments, Sarasota, FL). TEER values of the cell monolayer were approximately 250 Ω cm² after correcting for the resistance imparted by filters. [$^{14}$C]mannitol transport was <0.5%/h ($P_{app}$ <2 ×10$^{-7}$ cm s$^{-1}$) across the cell monolayer.

EXAMPLE 4

Stability Studies in Cell Homogenates and DPBS

Confluent MDCKII-MDR1 cells were washed three times with Dulbecco's phosphate buffered saline (DPBS) (130 mM NaCl, 7.5 mM Na$_2$HPO$_4$, 1.5 mM KH$_2$PO$_4$, 0.5 mM MgSO$_4$, 1 mM CaCl$_2$, 0.03 mM KCl and 5 mM glucose). Cells were then isolated with the aid of a mechanical scrapper and suspended in two volumes of water and homogenized (Multipro variable speed homogenizer, DREMEL; Racine, Wis.). Suitable dilutions were made to achieve a final protein concentration of 0.25 mg/mL. Protein content was determined according to the method of Bradford (Bradford, *Anal. Biochem.*, 72, 248 (1976)) with BioRad protein estimation kit.

An aliquot (800 µL) of the cell homogenate was incubated with 200 µL (30 µg/mL) prodrug solution at 37° C. in a shaking water bath (60 rpm). One hundred microlitres samples were withdrawn at predetermined time points and an equal volume of ice-cold acetonitrile:methanol (5:4) mixture was added to stop the enzymatic reaction. Samples were stored at −80° C. until further analysis.

Stability in DPBS was determined by incubating 200 µL prodrug solution with 800 µL DPBS with pH adjusted to 5 and 7.4. Slope of the line of "log percentage prodrug remaining versus time" plot was employed to calculate the degradation rate constants.

Stability of Val-Val-SQV and Gly-Val-SQV was determined in MDCKII-MDR1 cell homogenates, DPBS, pH 5, and DPBS, pH 7.4, for 48 h. Half-lives ($t_{1/2}$) of Gly-Val-SQV in MDCK-MDR1 cell homogenates, DPBS, pH 5, and DPBS, pH 7.4, were 1.75±0.11, 34.5±0.85 and 13.1±0.33 h, respectively. The half-life of Val-Val-SQV, in MDCK-MDR1 cell homogenates, DPBS, pH 5, and DPBS, pH 7.4, are 6.6±0.56, 94.8±21.4 and 18.3±1.4 h, respectively. Degradation studies suggest that some percentage of SQV is generated from the prodrugs during the uptake and transport experiments. Appreciable degradation was not observed for SQV in buffer and MDCKII-MDR1 cell homogenate.

EXAMPLE 5

Uptake Studies of Quinidine Derivatives in MDCKII-MDR1 Cells

In typical uptake experiments, cell monolayers grown on twelve well plates are incubated with non-radioactive drug/derivative solutions prepared in DPBS at pH 7.4 for 20 minutes. Cells are then rinsed with DPBS and cellular uptake of selected radioactive compounds (0.5 µCi) is performed in the presence of drug/derivative for the selected time period. Following incubation, the cell monolayers are rinsed three times with ice-cold HEPES buffer to terminate the uptake experiment. Then the cells are lysed overnight using 1 ml 0.1% (w/v) Triton X-100 in 0.3 N NaOH per well at room temperature. Aliquots (500 µl) from each well are then transferred to scintillation vials containing 5 ml scintillation cocktail (Fisher Scientific, Fairlawn, N.J.). Samples are then analyzed by the liquid scintillation spectrophotometry using a Beckman scintillation counter and the rate of uptake is normalized to the protein content of each well. The amount of protein in the cell lysate is measured by the BioRad protein estimation kit using bovine serum albumin as standard (BioRad Protein estimation Kit, Hercules, Calif.).

Figure 3:
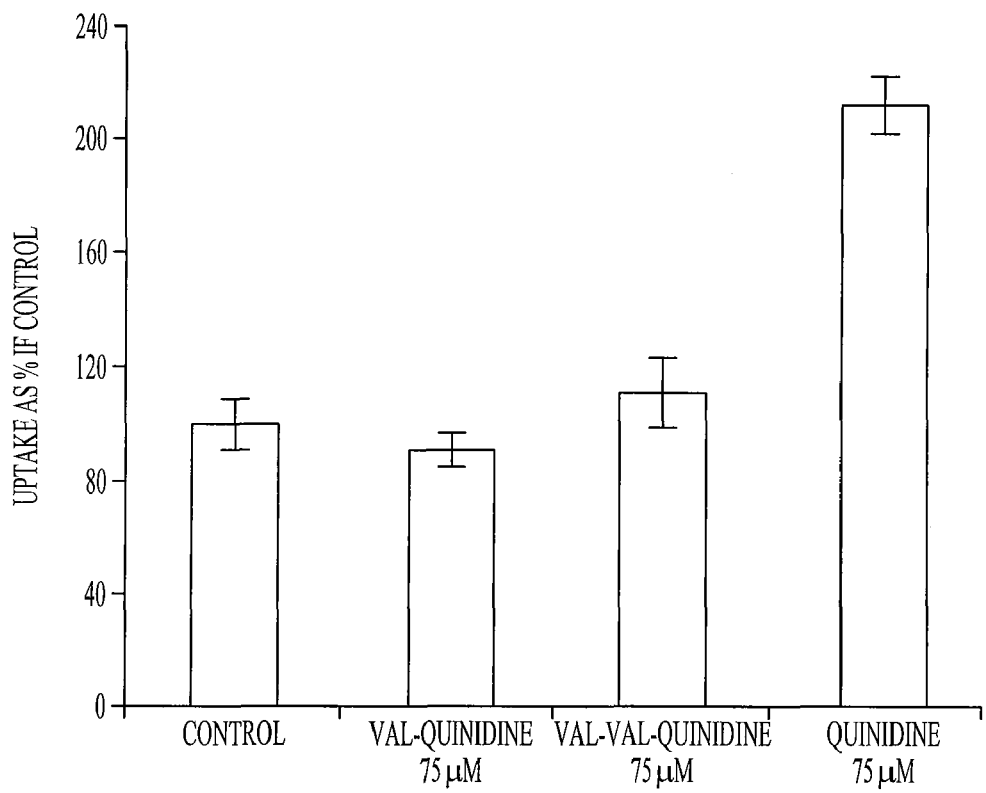
FIG. 3 is a plot of the uptake of [$^3$H] ritonavir by MDCKII-MDR1 cells in the presence of quinidine, val-quinidine, and val-val-quinidine.

Experiments were carried out to investigate the interaction of a model P-gp substrate [$^3$H]ritonavir with quinidine and its derivatives Val-Quinidine (Val-Q) and Val-Val-Quinidine (Val-Val-Q). FIG. 3 shows a two fold increase in ritonavir uptake in the presence of quinidine. However, [$^3$H]ritonavir uptake was not altered in the presence of equimolar concentration of val-quinidine and val-val-quinidine, suggesting that the peptide and amino acid derivatives of quinidine are not substrates of P-glycoprotein.

Figure 4:
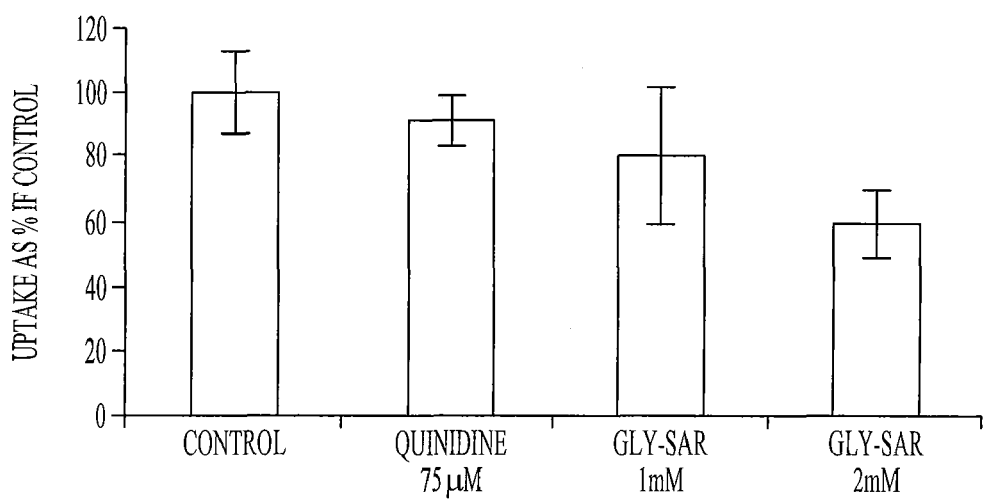
FIG. 4 is a plot of the uptake of [$^3$H] Glycyl-Sarcosine (Gly-Sar) (0.5 μCi/ml) by MDCKII-MDR1 cells in the presence quinidine and 1 mM and 2 mM unlabeled Gly-Sar.
Figure 5:
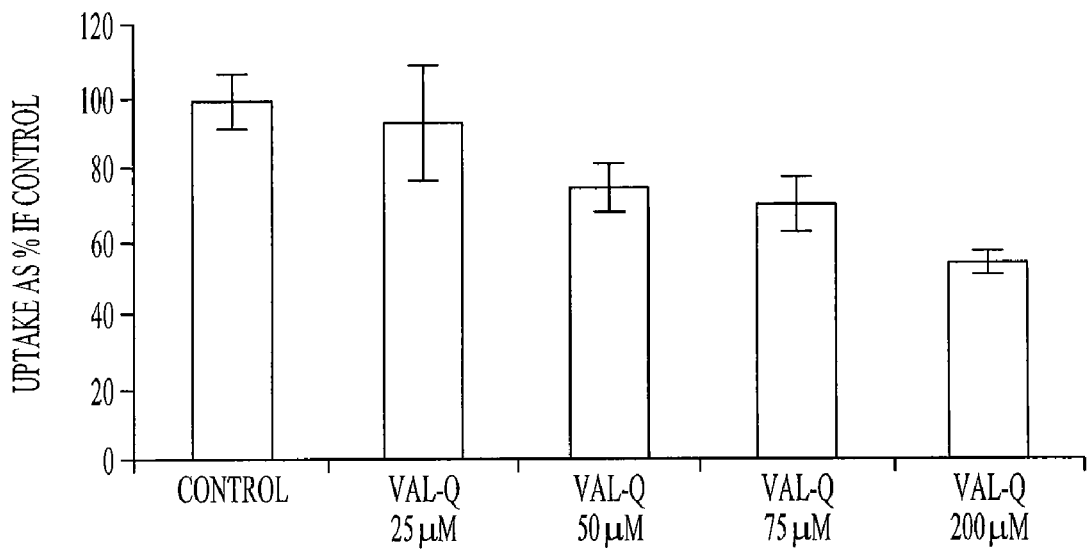
FIG. 5 is a plot of the uptake of [$^3$H] Gly-Sar (0.5 μCi/ml) by MDCKII-MDR1 cells in the presence of Val-Quinidine (Val-Q), a derivative according to the present invention.
Figure 6:
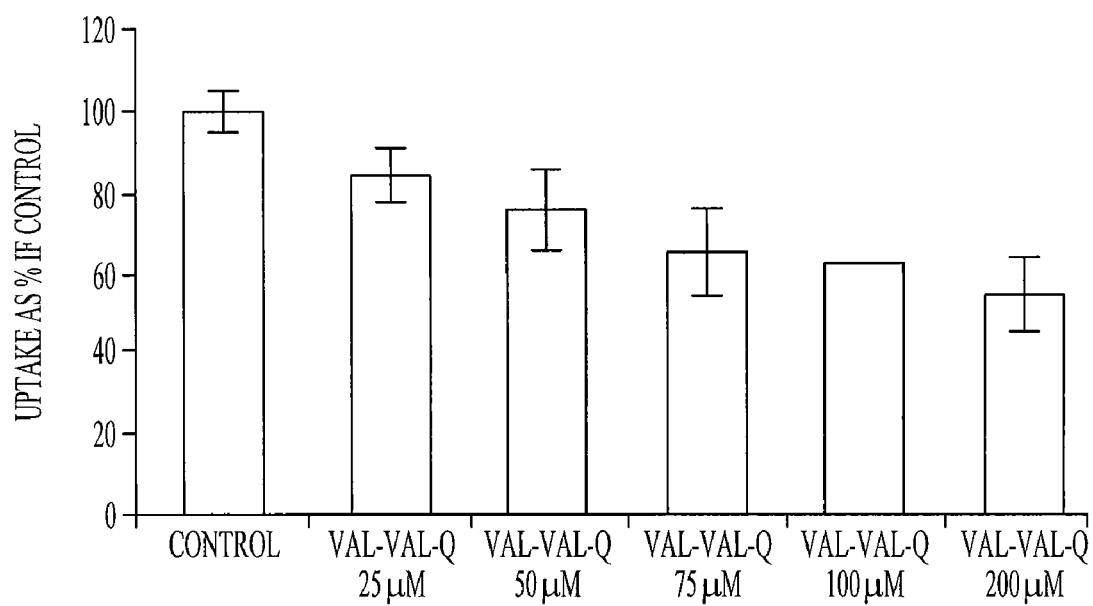
FIG. 6 is a plot of the uptake of [$^3$H] Gly-Sar (0.5 μCi/ml) by MDCKII-MDR1 cells in the presence of Val-Val-Quinidine (Val-Val-Q), a derivative according to the present invention.

Studies were performed to investigate whether derivatives of quinidine are substrates for a nutrient peptide transport system. Uptake studies of [$^3$H]Glycyl-Sarcosine (Gly-Sar) alone or in the presence of unlabeled Gly-Sar and in the presence of two derivatives of quinidine were carried out. Uptake of [$^3$H]Gly-Sar, in the presence of unlabeled Gly-Sar, at concentrations of 1 mM and 2 mM, demonstrated a concentration dependent decrease in cellular accumulation of [$^3$H]Gly-Sar. A significant decrease in cellular uptake in the presence of unlabeled Gly-Sar (FIG. 4) suggests expression of peptide transporters on the apical membrane of MDCKII-MDR1 cells. Val-quinidine and val-val-quinidine also demonstrated concentration dependent inhibition of [$^3$H]Gly-Sar uptake (FIGS. 5 and 6) suggesting that both derivatives are excellent substrates for the peptide transporter. Quinidine did not demonstrate any inhibition indicating that it is not interacting with peptide transporter.

EXAMPLE 6

Uptake Studies of Saquinavir Derivatives in MDCKII-MDR1 Cells

Uptake of [$^3$H]erythromycin, a well known P-gp substrate, was carried out at 0.25 µCi/mL in the presence of equimolar concentrations of saquinavir and its derivatives Val-SAQ, Val-Val-SAQ, and Gly-Val-SAQ as inhibitors (75 µM).

Figure 7:
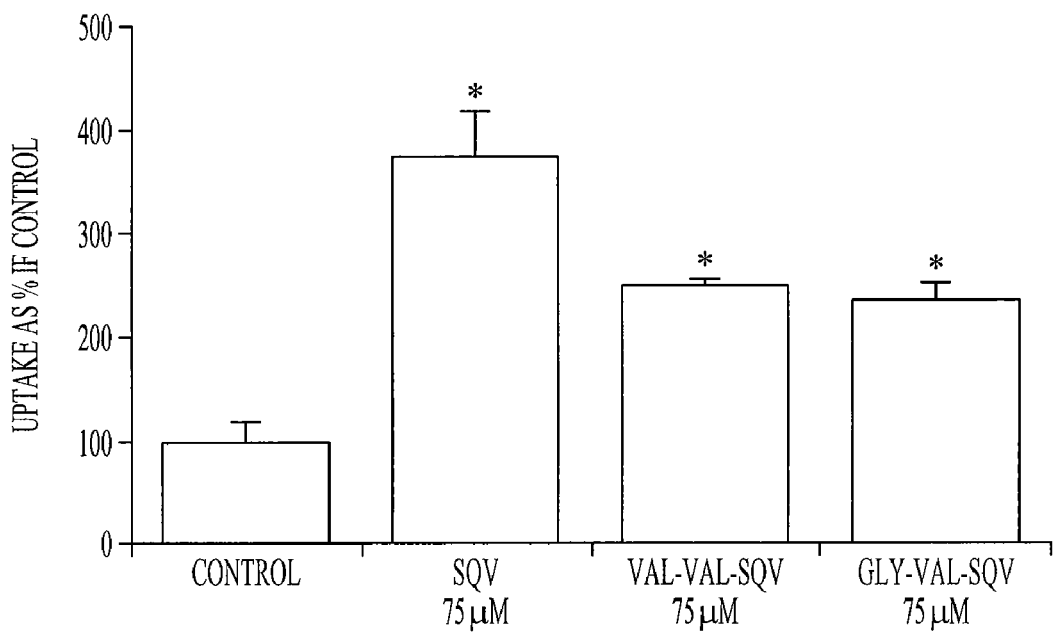
FIG. 7 is a plot of the uptake of [$^3$H] erythromycin (0.5 μCi/ml) by MDCKII-MDR1 cells in the presence of saquinavir and its derivatives according to the present invention.
Figure 8:
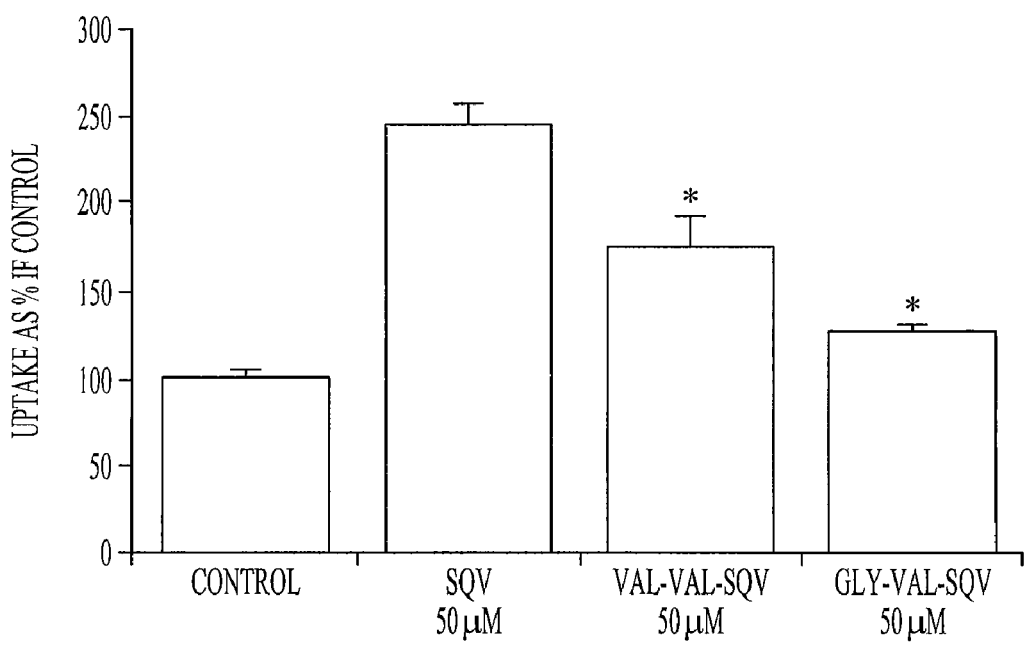
FIG. 8 is a plot of the uptake of [$^3$H] ritonavir (0.5 μCi/ml) by MDCKII-MDR1 cells in the presence of saquinavir and its derivatives according to the present invention.

Uptake of [$^3$H]erythromycin (0.25 µCi/mL), by MDCKII-MDR1 cells, was studied in the presence of equimolar concentration of SQV, Val-Val-SQV and Gly-Val-SQV (75 µM). A four-fold increment in the cellular uptake of [$^3$H]erythromycin was observed in the presence of 75 µM SQV. However, equimolar concentrations of SQV prodrugs produced only 2.5-fold increase in cellular uptake of [$^3$H]erythromycin (FIG. 7). These results indicate that prodrug modification results in decreased affinity of the prodrug molecule for the efflux transporter. Similar studies were carried out with [$^3$H] ritonavir (0.5 µCi/mL) as a P-gp substrate and SQV and its prodrugs as inhibitors. The results demonstrate that greatest inhibition was seen with SQV confirming our earlier observation that peptide prodrugs of SQV have reduced affinity for the efflux pump, P-gp (FIG. 8).

Uptake studies of SQV and the prodrugs were conducted with confluent MDCKII-MDR1 cell monolayers, 6-8 days post seeding. Medium was aspirated and cells were washed three times with DPBS, pH 7.4. SQV, Val-Val-SQV and Gly-Val-SQV solutions were prepared immediately before the experiment. Concentrated stock solution of SQV and the prodrugs were prepared in DMSO. Test solutions were prepared by diluting with DPBS, pH 7.4. Final DMSO concentration in all experiments was maintained constant and did not exceed 0.5% (v/v).

Uptake was initiated by adding 1 mL of drug solution (in the presence or absence of competing substrates) to the wells. Incubation was carried out over a period of 10 min at 37° C. At the end of the incubation period, the drug solution was removed and the cell monolayer was washed three times with ice-cold stop solution. Cells were lysed overnight (1 mL 0.1%, w/v, Triton X-100 in 0.3 N sodium hydroxide) at room temperature.

Aliquots (500 μL) were withdrawn from each well and transferred to scintillation vials containing 5 mL scintillation cocktail. Samples were then analyzed by liquid scintillation spectrophotometry with a Beckman scintillation counter (Model LS-6500, Beckman Instruments, Inc.). Uptake was normalized to the protein content of each well. Amount of protein in the cell lysate was quantified by the method of Bradford utilizing BioRad protein estimation kit (BioRad, Hercules, Calif.).

Figure 9:
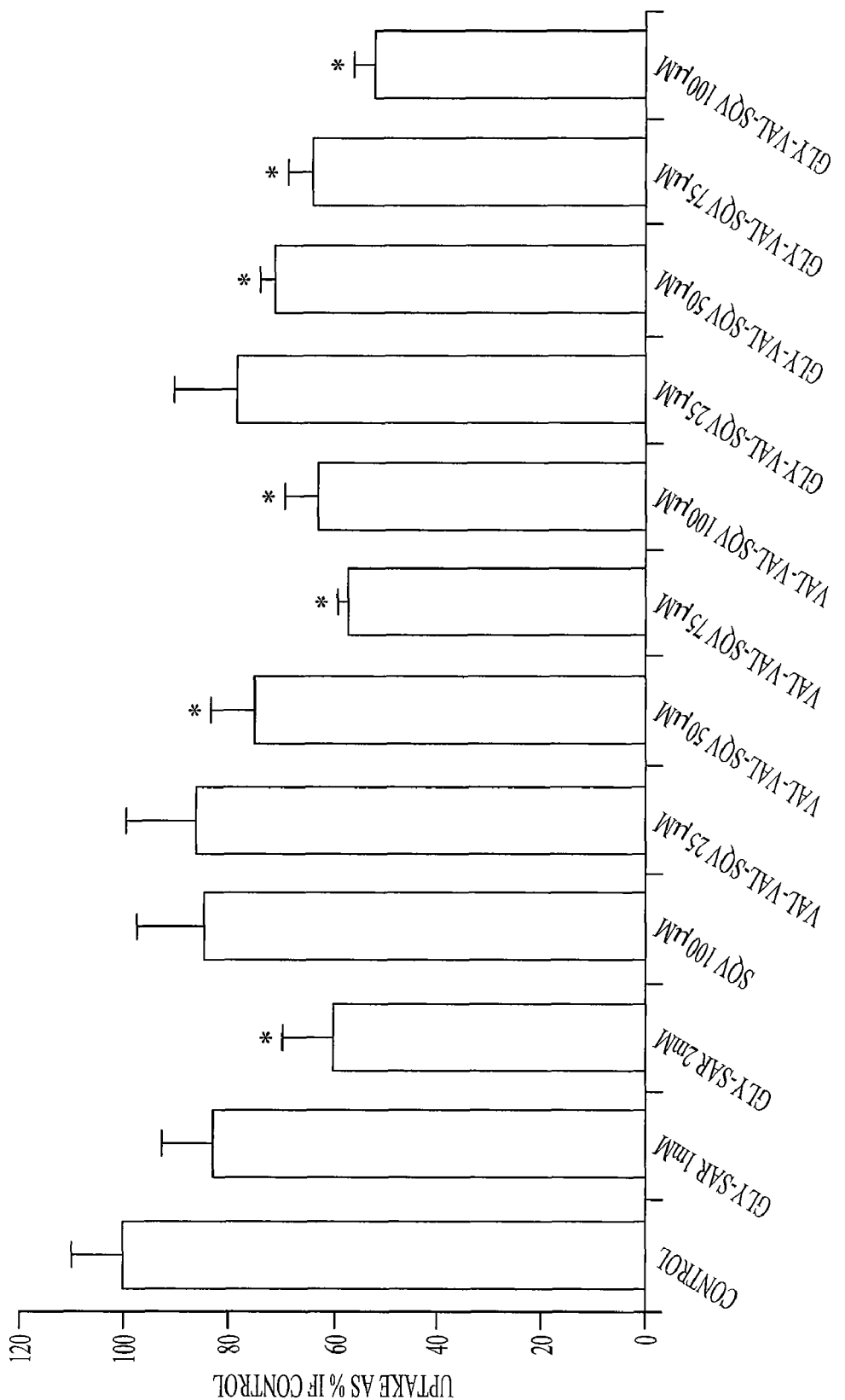
FIG. 9 is a plot of the uptake of [$^3$H]Gly-Sar (0.5 μCi/mL) by MDCKII-MDR1 cells in the absence (control) or present of 1 and 2 mM unlabeled Gly-Sar, SQV (100 μM), different concentrations of Gly-Val-SQV and Val-Val-SQV. *p<0.05 represents statistically significant difference as compared to control. Data expressed as mean±S.D. (n=4).

Uptake of [$^3$H]Gly-Sar (0.5 μCi/mL), in the presence of unlabeled Gly-Sar, at concentrations of 1 and 2 mM, demonstrated a concentration dependent reduction in cellular accumulation of [$^3$H]Gly-Sar. Unlabeled Gly-Sar at concentrations of 1 and 2 mM reduced the uptake of [$^3$H]Gly-Sar from 0.033 to 0.026 pmol/(min mg) (20%) and 0.019 pmol/(min mg) (41%), respectively (FIG. 9). Uptake of [$^3$H]Gly-Sar was significantly decreased in the presence of Val-Val-SQV (100 μM) and Gly-Val-SQV (100 μM), whereas equimolar concentration of SQV did not demonstrate any significant inhibition on [$^3$H]Gly-Sar uptake (FIG. 9). All the prodrugs exhibited concentration dependent inhibition of [$^3$H]Gly-Sar uptake (FIG. 9). Higher percentage inhibition of [$^3$H]Gly-Sar uptake by SQV prodrugs, compared to equimolar concentrations of unlabeled Gly-Sar, indicates that SQV prodrugs may possess even higher affinity for the peptide transporter compared to Gly-Sar, a well known peptide transporter substrate.

EXAMPLE 7

Drug Transport Studies of Quinidine and its Derivatives Across MDCKII-MDR1 Cells Transport studies were conducted with MDCKII-MDR1 cell monolayers grown on 12-well Transwell® inserts (12 mm diameter). The medium was aspirated, and cell monolayers were washed three times (10 minutes per wash) with DPBS (pH 7.4). Volumes of the apical and basolateral chambers were 0.5 and 1.5 ml, respectively. Transport experiments were conducted for a period of 3 hours. Aliquots (200 μl) were withdrawn at predetermined time intervals, i.e., 15, 30, 45, 60, 90, 120, 150, and 180 minutes and replaced with fresh DPBS (pH 7.4) to maintain sink conditions. Samples were stored at −80° C. until further analysis. Experiments designed to investigate the effect of inhibitors involved preincubation of the cells with the inhibitor for a period of 30 minutes (inhibitor solution was added to both donor and receiver chambers) prior to the addition of the drug solution (also containing the inhibitor) to initiate the transport study. All transport experiments were performed at 37° C.

Quinidine and val-quinidine samples were assayed by reversed phase high performance liquid chromatography (HPLC). The HPLC system comprised an HP 1050 pump, an Agilent 1100 series fluorescence detector, and an Alcott autosampler (model 718 HPLC). A C(8) Luna coumn (250 mm×4.6 mm); Phenomenex, Torrance, Calif. was employed in the analysis. The mobile phase consisted of 20 mM phosphate buffer (pH adjusted to 2.5) and 12% acetonitrile as the organic modifier. The parent drug and the derivative were detected with a fluorescence detector ($\lambda_{ex}$=240 nm, $\lambda_{em}$=450 nm). Val-quinidine eluted at approximately 6 minutes, while quinidine eluted at 7 minutes.

Cumulative amount of val-quinidine and quinidine transported across the cell monolayers were plotted as a function of time to determine the permeability coefficient. Linear regression analysis of the amounts transported as a function of time yielded the rate of transport across the cell monolayer (dM/dt). The rate divided by the cross-sectional are available for transport (A) generated the steady-state flux as shown in Equation 1.

flux=(dM/dt)/A     (Equation 1)

Permeability was calculated by normalizing the steady-state flux to the donor concentration ($C_d$) of the drug according to Equation 2.

Permeability=flux/$C_d$     (Equation 2)

Figure 10:
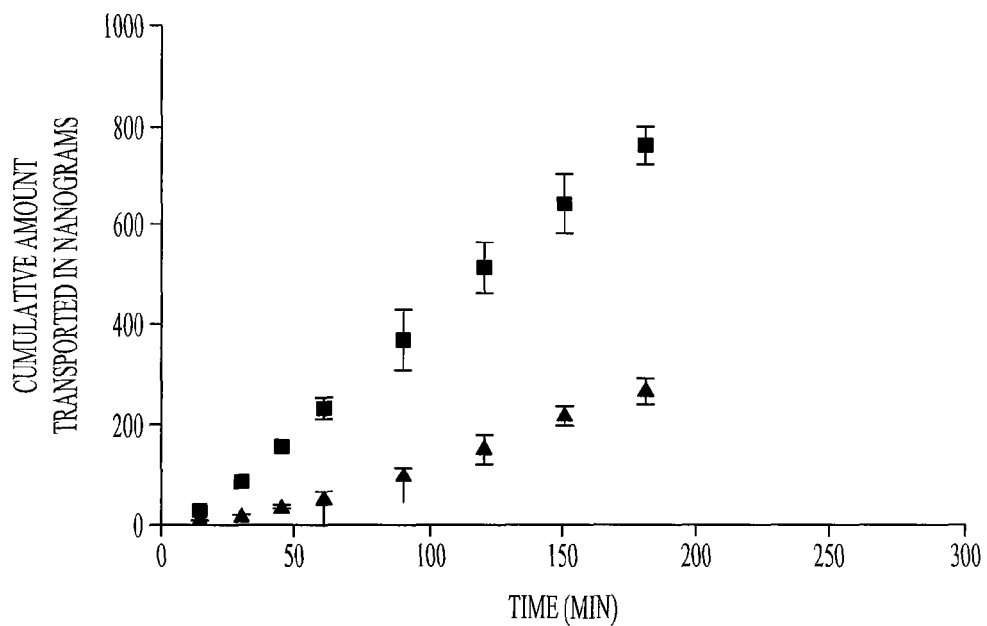
FIG. 10 is a plot of bidirectional transepithelial transport of quinidine (10 μM) across MDCKII-MDR1 cell monolayers: ▲ apical to basolateral (AP-BL) direction; ■, basolateral to apical (BL-AP) direction.
Figure 11:
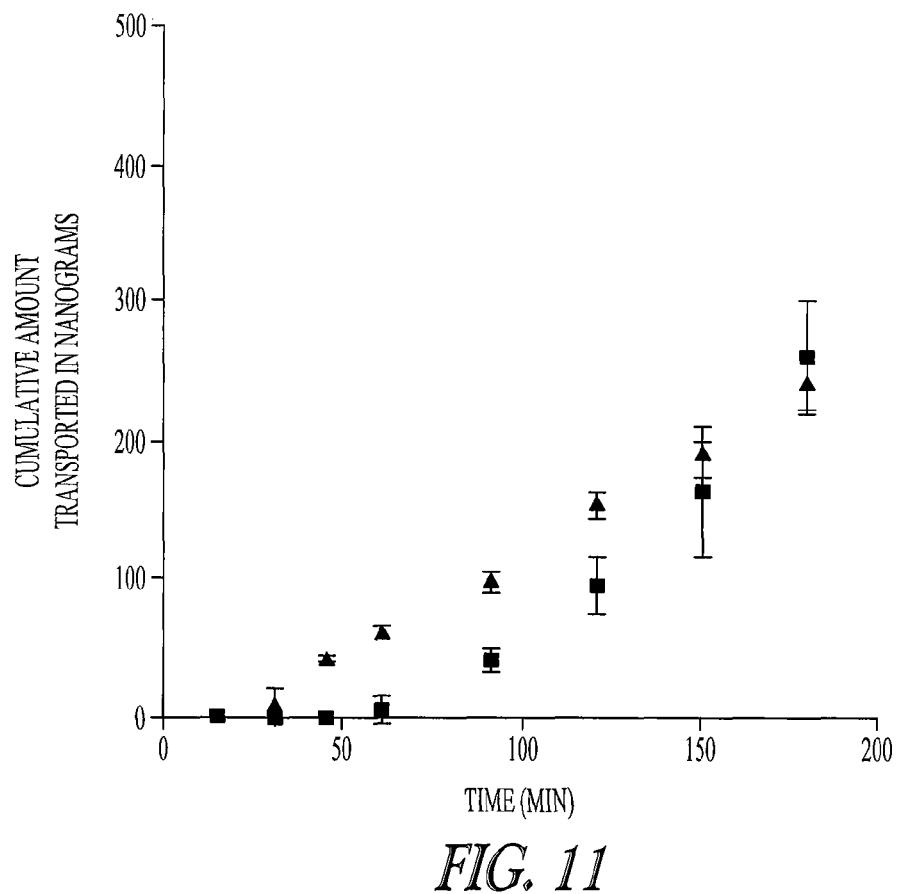
FIG. 11 is a plot of bidirectional transport of val-quinidine (10 μM) across MDCKII-MDR1 cell monolayers. ▲ apical to basolateral (AP-BL) direction; ■ basolateral to apical (BL-AP) direction.

A classical example of P-gp involvement in transport kinetics is the difference in permeation rates of P-gp substrates in the apical to basolateral and basolateral to apical directions. If a compound is a substrate for P-gp the apical to basolateral transport (AP-BL) is considerably lower than that from the basolateral to apical direction (BL-AP) because of enhanced efflux in the BL-AP direction. Transepithelial bi-directional transport of quinidine across MDCKII-MDR1 cells revealed that the transepithelial transport of quinidine in the absorptive direction (AP to BL), was significantly lower than that in secretory (BL to AP) direction (FIG. 10). Apparent permeability of quinidine (10 μM) $P_{app}$ in the AP-BL was 6.5±0.66× $10^{-6}$ cm.s$^{-1}$ and BL-AP direction was 18.3±1.25×$10^{-6}$ cm.s−1 with a three fold difference. Relative to quinidine, permeability of Val-Q from AP to BL and BL to AP direction was equivalent. Val-Q permeability from AP to BL direction was 5.13±0.49×$10^{-6}$ cm.s$^{-1}$ and from BL to AP direction was 6.17±1.28×$10^{-6}$ cm.s$^{-1}$ (FIG. 11). These results confirm that asymmetric permeation of pure quinidine across the cell monolayer is attributable to the efflux activity of P-gp, whereas val-quinidine is not being effluxed by P-gp. The permeability rates of val-quinidine in both directions are very similar.

EXAMPLE 8

Drug Transport Studies of SAQ and its Derivatives Across MDCKII-MDR1 Cells

A. Procedures

Transport studies with MDCKII-MDR1 cell monolayers were carried out as described in Example 7. Concentrations used in the bidirectional studies were SQV, 10 μM; Gly-Val-SQV, 20 μM; Val-Val-SQV, 22 μM. Detection issues of the prodrug and/or parent drug in the acceptor chamber was considered for the selection of prodrug concentration. Aliquots (200 μL) were withdrawn at predetermined time intervals, i.e., 15, 30, 45, 60, 90, 120, 150, 180 min, respectively, and replaced with fresh DPBS, pH 7.4, to maintain sink conditions. Dilutions were taken into account for the calculations. Samples were stored at −80° C. until further analysis. All transport experiments were performed at 37° C.

SQV, Val-Val-SQV and Gly-Val-SQV samples were analyzed by a reversed phase HPLC technique (Ucpinar, Biomed. Chromatogr., 13, 21 (2003)). The HPLC system was comprised of HP 1050 pump, Waters dual wavelength absorbance UV detector, and an Alcott auto sampler (model 718AL HPLC). A C(8) Luna column (250 mm×4.6 mm; Phenomenex, Torrance, Calif.) was employed for the separation of analytes. Mobile phase composed of acetonitrile:water:triethylamine (55:44:1%, v/v/v) and the pH was adjusted to 6.5 with o-phosphoric acid. Flow rate was maintained at 0.8 mL/min and detection wavelength was set at 240 nm. Elution times for SQV, Gly-Val-SQV and for Val-Val-SQV were 8, 6 and 12 min, respectively.

All experiments were conducted at least in quadruplicate (n=4) and results are expressed as mean±S.D. Statistical comparison of mean values were performed with one-way analysis of variance (ANOVA) or Student's t-test (Graph Pad INSTAT, Version 3.1). *$p<0.05$ was considered to be statistically significant.

B. Transport of SQV Across MDCKII-MDR1 Cells

Figure 12:
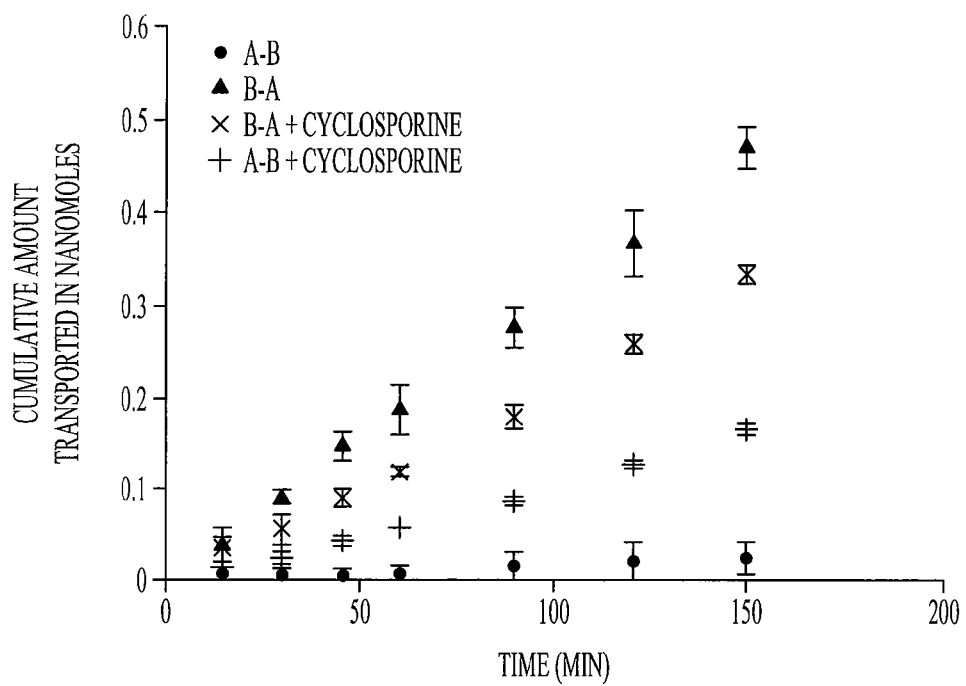
FIG. 12 is a plot of the transepithelial transport of saquinavir (10 μM) across MDCKII-MDR1 cell monolayers: ●, apical to basolateral (AP-BL) direction; ▲, basolateral to apical (BL-AP) direction, (+) AP-BL transport in the presence of cyclosporine; (x) BL-AP transport in the presence of cyclosporine. Values are expressed as mean±S.D. (n=4).

Transepithelial bidirectional transport of SQV across MDCKII-MDR1 cells demonstrates that transport of SQV in the absorptive direction (AP-BL) direction, was significantly lower ($p<0.05$) than that in secretory (BL-AP) direction (FIG. 12). Apparent permeability ($P_{app}$) of SQV from BL to AP direction was $1.99\pm0.17\times10^{-5}$ and from AP to BL direction was $4.63\pm0.25\times10^{-7}$ cm s$^{-1}$ a 40-fold difference. This asymmetric permeation is due to the involvement of the apically polarized P-gp efflux transporter, for which SQV is a very good substrate. In the presence of 10 µM cyclosporine, secretory permeability ($P_{app}$) of SQV significantly reduced from $1.99\pm0.17\times10^{-5}$ to $1.33\pm0.06\times10^{-5}$ cm s$^{-1}$ and absorptive permeability increased from $4.63\pm0.25\times10^{-7}$ to $6.80\pm0.34\times10^{-6}$ (FIG. 12).

C. Transport of Val-Val-SQV and Gly-Val-SQV Across MDCKII-MDR1 Cells

Transepithelial transports of Val-Val-SQV and Gly-Val-SQV were studied across MDCKII-MDR1 cell monolayers. During the transport process degradation of prodrug can take place in the transport buffer (in the donor compartment), cell cytoplasm (when the drug molecule diffuses inside the cell) or in the receiver chamber after the drug has been transported. In vitro stability studies of the prodrugs involving transport buffers and cell homogenates demonstrate that some quantity of SQV can be regenerated during the transport process. During the transport of Val-Val-SQV and Gly-Val-SQV hydrolysis products, Val-SQV and SQV, were observed. Intact prodrug transported and breakdown products, formed during the transport study, were analyzed. Cumulative amount of drug transported (the sum of prodrug and regenerated parent drug) was plotted as a function of time. Apparent permeabilities ($P_{app}$) were determined from the linear portion of the cumulative amount versus time plot.

Figure 13:
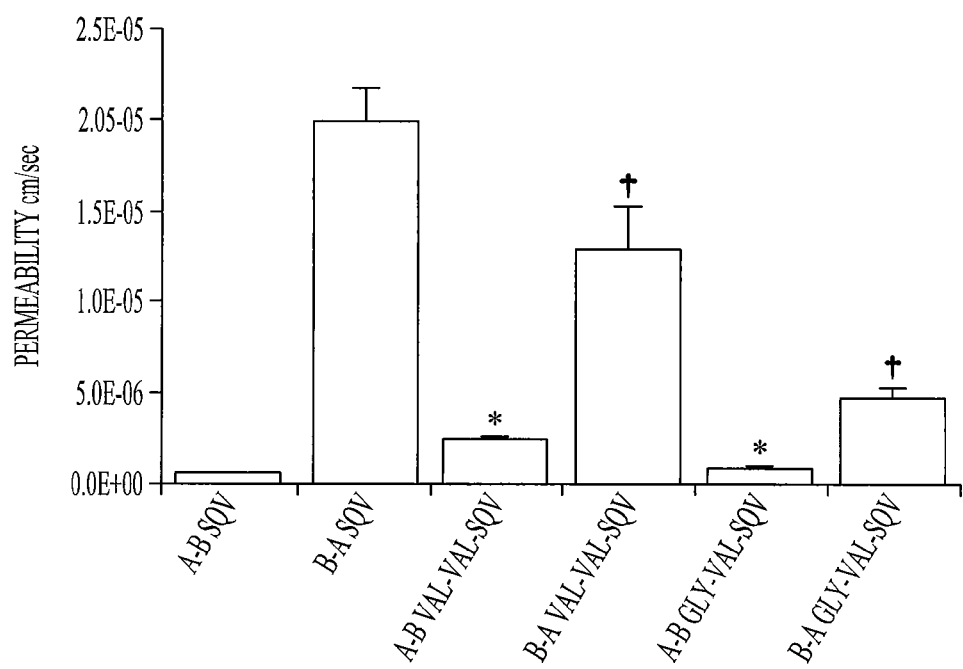
FIG. 13 is a plot of the apparent permeability of SQV, Val-Val-SQV and Gly-Val-SQV in apical to basolateral direction and basolateral to apical direction across MDCK-MDR1 cells. A statistically significant difference (*p<0.05) in AP-BL direction and (*p<0.05) in BL-AP direction as compared to SQV was observed.

AP-BL permeabilities of SQV from Val-Val-SQV ($2.39\pm0.16\times10^{-6}$ cm s$^{-1}$) and Gly-Val-SQV ($7.67\pm1.04\times10^{-7}$ cm s$^{-1}$) were enhanced significantly as compared to that of SQV ($4.63\pm0.25\times10^{-7}$ cm s$^{-1}$) (FIG. 13). Similarly, BL-AP permeabilities of SQV from Val-Val-SQV ($1.28\pm0.23\times10^{-5}$ cm s$^{-1}$) and Gly-Val-SQV ($4.72\pm0.59\times10^{-6}$ cm s$^{-1}$) were significantly lower than SQV ($1.99\pm0.17\times10^{-5}$ cm s$^{-1}$) (FIG. 13). Such enhanced AP-BL transport of SQV prodrugs can be attributed to an active transport mechanism and/or decreased efflux resulting from reduced affinity of these prodrugs for P-gp. These results are consistent with earlier observations that SQV increases cellular uptake of [$^3$H]erythromycin and [$^3$H]ritonavir to a greater extent relative to prodrugs.

D. Transport of Val-Val-SQV in Presence of Gly-Sar

Figure 14:
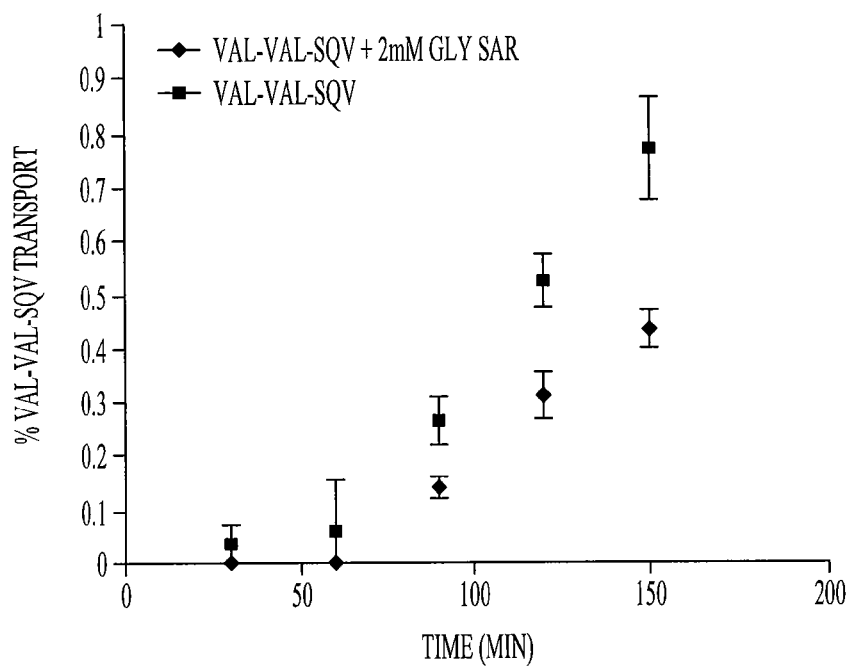
FIG. 14 is a plot of the percentage transport of Val-Val-SQV in the presence of 2 mM Gly-Sar across MDCK-MDR1 cells.

Transport of Val-Val-SQV was conducted in the presence of 2 mM Gly-Sar across MDCK-MDR1 cells. Significant inhibition in Val-Val-SQV transport was observed in presence of 2 mM Gly-Sar (FIG. 14). A two-fold reduction in total percentage Val-Val-SQV transported, at the end of 150 min, was observed in the presence of Gly-Sar.

E. Discussion

Cellular uptake of [$^3$H]erythromycin showed a four-fold enhancement in the presence of SQV, whereas an equimolar concentration of Val-Val-SQV and Gly-Val-SQV demonstrated only 2.5-fold increment in [$^3$H]erythromycin uptake (FIG. 7). This differential inhibition by equimolar concentration of SQV and its derivatives indicates that the dipeptide prodrugs have reduced affinity for P-gp. Similar results were obtained when cellular uptake of [$^3$H]ritonavir was determined in the presence of equimolar concentrations of SQV and its prodrugs.

Uptake of [$^3$H]erythromycin was studied in the presence of 75 µM Val-Val-SQV and Gly-Val-SQV, whereas [$^3$H]ritonavir uptake was evaluated in the presence of 50 µM of the prodrugs. Two different concentrations were employed to examine the effect of prodrug concentration on P-gp inhibition.

Concentration dependent uptake studies demonstrated that Val-Val-SQV saturates P-gp at 50 µM, whereas Gly-Val-SQV saturates P-gp at 75 µM. Consequently, when used at 75 µM both prodrugs exhibit similar extent of inhibition, whereas, differential inhibition is observed at lower concentrations (FIG. 7 and FIG. 8).

Furthermore, uptake studies were conducted to study whether the SQV prodrugs are substrates for peptide transporters. Uptake of [$^3$H]Gly-Sar (0.5 µCi/mL), in the presence of unlabeled Gly-Sar, at concentrations of 1 and 2 mM, demonstrated a concentration dependent decrease in cellular accumulation of [$^3$H]Gly-Sar. Such diminished cellular uptake in the presence of unlabeled Gly-Sar suggests expression of peptide transporters on the apical membrane of MDCKII-MDR1 cells (FIG. 9).

This is consistent with earlier reports on the expression of peptide transporters on MDCK cells (Putnam et al., *J. Pharm. Sci.*, 91, 2622 (2002)). Uptake of [$^3$H]Gly-Sar was also reduced by 35% in the presence of 100 µM Val-Val-SQV and by 42% in the presence of 100 µM Gly-Val-SQV. However, equimolar concentration of SQV did not demonstrate any inhibition of [$^3$H]Gly-Sar uptake (FIG. 9). Also, Val-Val-SQV and Gly-Val-SQV demonstrated concentration dependent inhibition of [$^3$H]Gly-Sar uptake exhibiting highest inhibition at 100 µM (FIG. 9).

Greater percentage inhibition of [$^3$H]Gly-Sar uptake by prodrugs, compared to equimolar concentrations of unlabeled Gly-Sar, indicates that prodrugs may possess higher affinity for the peptide transporter relative to Gly-Sar. Several earlier reports indicated that valine ester prodrugs are substrates of peptide transporters, e.g., valine esters of ganciclovir (Sugawara et al., *J. Pharm. Sci.*, 89, 781 (2000)) and acyclovir (Balimane et al., *BBRC*, 250, 246 (1998)) which resulted in increased oral bioavailability of the parent drugs.

High transport capacity, broad substrate specificity and dense expression of peptide transporter in intestine and other biological barriers render the peptide transporter an ideal candidate for drug targeting. These results suggest that compounds of the invention such as Val-Val-SQV and Gly-Val-SQV may be excellent substrates for the peptide transporter expressed on apical membrane of MDCKII-MDR1 cells, whereas SQV is not.

To further test the hypothesis that prodrug modification can bypass P-gp mediated efflux and increase absorption, transepithelial transport studies were conducted employing MDCK-MDR1 cells. A classical indication of P-gp involvement in transport kinetics is the difference in permeation rates of P-gp substrates in the apical to basolateral and basolateral to apical directions (Polli et al., *J. Pharmacol. Exp. Ther.*, 299, 620 (2001)). If a compound is a substrate for P-gp, apical to basolateral transport (AP-BL) is considerably lower than that from the basolateral to apical direction (BL-AP).

Transepithelial bi-directional transport studies of SQV across MDCKII-MDR1 cells revealed that transport studies of SQV in the absorptive direction (AP-BL) direction, was significantly lower than that in secretory (BL-AP) direction with an efflux ratio (BL $P_{app}$/AP $P_{app}$) of 40 (FIG. 8). This asymmetric permeation is due to the presence of apically polarized P-gp efflux pump, for which SQV is a very good substrate. In the presence of 10 μM cyclosporine, a P-gp inhibitor, secretory permeability ($P_{app}$) of SQV was significantly decreased from $1.99\pm0.17\times10^{-5}$ to $1.33\pm0.06\times10^{-5}$ cm s$^{-1}$ and absorptive permeability increased from $4.63\pm0.25\times10^{-7}$ to $6.80\pm0.34\times10^{-6}$ (FIG. 8). Such decrease in secretory transport and increase in absorptive transport is due to the inhibitory effect of cyclosporine on P-gp mediated efflux of SQV.

Gly-Val-SQV and Val-Val-SQV also showed asymmetric SQV permeation across the cell monolayer however with a flux ratio of only 6. This decrease in efflux ratio of SQV prodrugs as compared to SQV (flux ratio 40) is attributed to increased absorptive flux (AP-BL) and decreased secretory flux (BL-AP). In vitro stability studies of the prodrugs involving transport buffers and cell homogenates demonstrate that some quantity of SQV can be regenerated during the transport process. Asymmetric permeability of SQV prodrugs is possibly due to SQV regeneration from the prodrugs (which is again a good substrate for P-gp) during the course of a transport study. Two- to five-fold increment in the absorptive permeability of the dipeptide prodrug is probably due to involvement of an active peptide transport system. A decrease in secretory permeability may be attributed to the lower affinity of these prodrugs for P-gp (Table 2).

TABLE 2

Apparent permeabilities ($P_{app}$) of SQV and its peptide prodrugs across MDCKII-MDR1 cells

| Compound | $P_{app}$ (AP-BL) (cm s$^{-1}$) | $P_{app}$ (BL-AP) (cm s$^{-1}$) |
|---|---|---|
| SQV | $4.63 \times 10^{-7}$ ($\pm0.25$) | $1.99 \times 10^{-5}$ ($\pm0.17$) |
| Val-Val-SQV | $2.39 \times 10^{-6}$ ($\pm0.16$) | $1.28 \times 10^{-5}$ ($\pm0.23$) |
| Gly-Val-SQV | $7.67 \times 10^{-7}$ ($\pm1.04$) | $4.72 \times 10^{-5}$ ($\pm0.59$) |
| SQV + cyclosporine | $6.80 \times 10^{-6}$ ($\pm0.34$) | $1.33 \times 10^{-5}$ ($\pm0.06$) |

As compared to SQV, Val-Val-SQV showed increased AP-BL and not much decrease in BL-AP transport which can be attributed to various factors such peptide transporter mediated translocation (FIG. 14), lower efflux by P-gp, higher lipophilicity and higher stability in the buffer and cell homogenates.

In contrast, Gly-Val-SQV showed marginal increase in AP-BL transport and tremendous decrease in BL-AP direction as compared to SQV, which can be attributed to its lower efflux by P-gp and lower lipophilicity (compared to both SQV and Val-Val-SQV). Additionally, the prodrugs may possess differential affinity for the basolateral peptide transporter, which may contribute towards the differences in AP-BL and BL-AP transport.

To further test the hypothesis that increased AP-BL transport of Val-Val-SQV was due to peptide transporter mediated influx, transport studies were conducted in presence of Gly-Sar. In presence of 2 mM Gly-Sar, there is a significant decrease in Val-Val-SQV transport (FIG. 14).

These results together with uptake results clearly show that SQV prodrugs not only bind to peptide transporter but also are translocated by the peptide transporter. Thus, peptide prodrug derivatization of SQV is a viable strategy to bypass P-gp mediated efflux such that the oral absorption of these poorly absorbed drugs can be significantly enhanced.

Ratio between prodrug affinity for the efflux pump and active nutrient transporter will determine whether a drug molecule can circumvent P-gp mediated efflux. If a molecule has greater affinity for nutrient transporter, then it will preferentially bind to the nutrient transporter and will be translocated across the cell membrane. Prodrug molecules are not freely available for binding to efflux pump and consequently P-gp fails to recognize the prodrug molecule and will result in the prodrug bypassing P-gp mediated efflux.

Circumventing P-gp mediated efflux will not only increase absorption across intestinal mucosa but will also decrease the repetitive exposure to metabolism in intestinal mucosa. In vitro data from these studies indicate that prodrug modification of SQV leads to partial avoidance of its P-gp mediated efflux, and enhanced absorption due to the involvement of nutrients transporters. Two- to five-fold enhancement in absorption of SQV through peptide prodrug design indicates that potentially lower doses can be administered orally to AIDS patients.

These examples demonstrate for the first time that peptide prodrug modification of SQV to Val-Val-SQV and Gly-Val-SQV can lead to an increased permeability across P-gp overexpressing MDCKII-MDR1 cells. This increase in permeability, under the experimental conditions employed, can be attributed partially to P-gp's failure to recognize these compounds as substrates, and partially due to involvement of peptide transport system. Thus, transporter targeted prodrug modification of P-gp substrates could lead to shielding of these drug molecules from efflux pump. This method is believed to be generally applicable, to lead to enhanced drug delivery across biological membranes expressing efflux pumps in general and particularly to enhance chemotherapy of drug resistant tumors.

EXAMPLE 9

Primary Culture of Rabbit Corneal Epithelial Cells (rPCEC)

Adult male New Zealand albino rabbits weighing between 2-2.5 kg were obtained from Myrtle's rabbitry, Thompson Station, TN. Rabbit corneas were excised and washed thoroughly with DPBS, blotted dry, and transferred to sterile culture dishes containing 0.5 ml trypsin (0.25%) or 1.2 U/ml protease (Dispase II, Roche Molecular Biochemical). The corneas were placed upside down (with the concave surface touching the protease solution) and incubated at 37° C. for 30 minutes. The epithelial cells were stripped off with gentle scraping from peripheral areas (1-1.5 mm from the limbus) to the center. Care was taken to peel only the epithelial layer and not the underlying stromal layer, because that would contaminate the epithelial cells with keratinocytes. Cells were washed with MEM (Life Technologies, Grand Island, N.Y.) and placed in culture dishes. After 12 hours (when most of the cells had attached to the bottom), the MEM was removed and fresh MEM supplemented with insulin (5 μg/ml), transferrin (5 μg/ml), sodium selenite (5 μg/ml), amphoterecin B (0.25 μg/ml), polymyxin B sulfate (0.5 μg/ml), penicillin (100 U/ml), streptomycin (100 μg/ml), human recombinant epidermal growth factor (10 μg/ml), and bovine pituitary extract (50 μg/ml) were added. The medium was changed twice a week, and the cells were subcultured every 7 to 10 days (subculture ratio, 1:5). Cells reached senescence by passages 7 to 10, and therefore passages 2 to 6 were used for all further experiments.

EXAMPLE 10

Uptake Studies of Quinidine Derivatives on rPCEC cells

Figure 15:
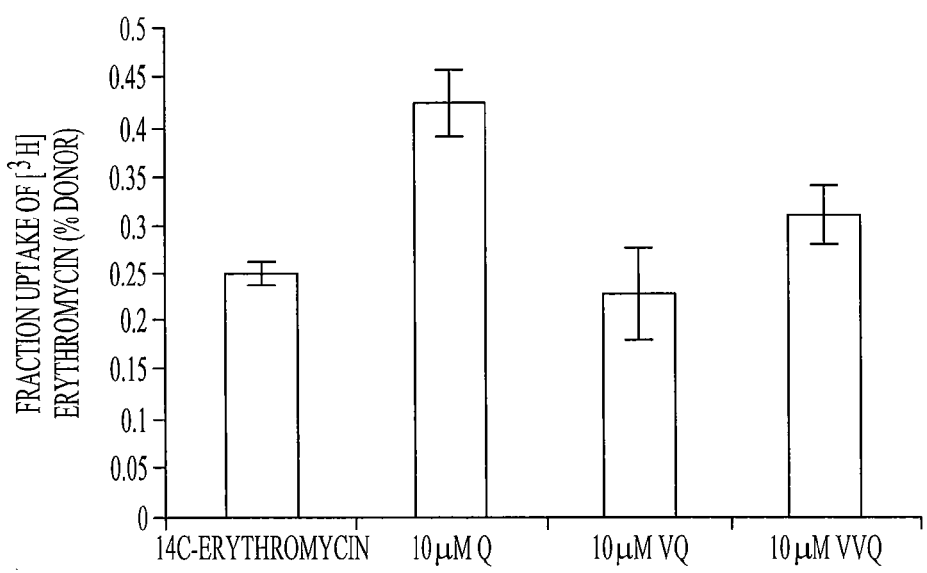
FIG. 15 is a plot of the uptake of [$^3$H] erythromycin (0.5 μCi/ml) by rPCEC cells in the presence of quinidine (Q) and its derivatives Val-Quinidine (Val-Q) and Val-Val-Quinidine (Val-Val-Q) according to the present invention.
Figure 16:
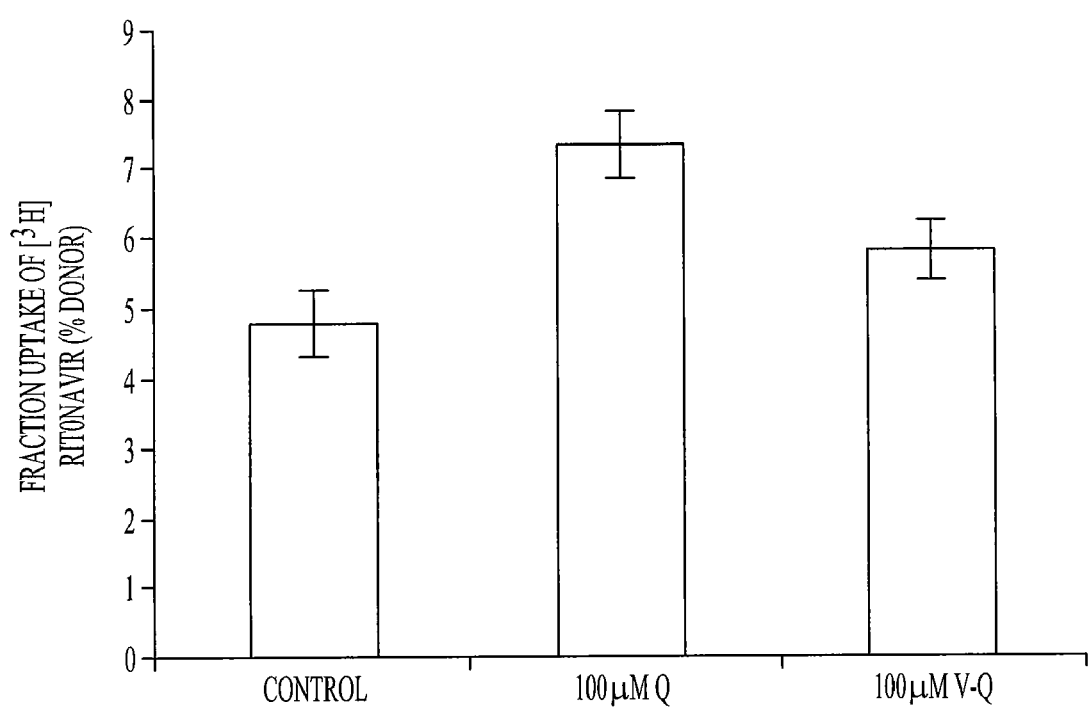
FIG. 16 is a plot of the uptake of [$^3$H] ritonavir (0.5 μCi/ml) by rPCEC cells in the presence of quinidine and its derivative Val-Quinidine (Val-Q).

Uptake of [$^3$H] erythromycin, a well known P-gp substrate, was carried out in the presence of equimolar concentrations of quinidine and its derivatives Val-Q and Val-Val-Q as inhibitors. Uptake of erythromycin revealed a high inhibitory effect on P-gp mediated efflux with quinidine as compared to its derivatives (FIG. 15). These results indicate that derivatization according to the present invention results in decreased affinity of the derivative molecule for the efflux transporter. Similar studies were carried out with [$^3$H] ritonavir as substrate and quinidine and its derivatives as inhibitors. The results demonstrate that highest inhibition was seen with quinidine, which confirms that the derivative molecules have reduced affinity for the efflux transporter P-gp (FIG. 16).

EXAMPLE 11

Absorption Studies of P-gp Substrates Across Rabbit Corneas In Vivo

Adult male New Zealand albino rabbits weighing between 2-2.5 kg were obtained from Myrtle's rabbitry, Thompson Station, Tenn. Throughout an experiment, the animals were kept under anesthesia with ketamine HCl (35 mg/kg) and xylazine (3.5 mg/kg) given intramuscularly every hour. Pupils were dilated with two drops of 1% tropicamide prior to implantation of microdialysis probes. Linear probes were implanted in the anterior chamber using 25-gauge needles. They were inserted across the cornea just above the corneal scleral limbus so that they traversed through the center of the anterior chamber to the opposite end of the cornea, as evidenced by microscopic examination. The sample-collecting end of the linear probe was inserted carefully into the beveled edge end of the needle. The needle was retracted slowly, leaving the probe in the dialyzing membrane in the middle of the anterior chamber. The outlets of the probes were fixed to prevent any disturbances during sample collection. The probes were perfused with isotonic IPBS (pH 7.4) at a flow rate of 2 µl/min using a CMA/100 microinjection pump. After probe implantation, the animals were allowed to stabilize for 2 hours prior to the initiation of any study. This duration has been shown to be sufficient for the restoration of intraocular pressure and replenishment of the aqueous humor originally lost during probe implantation (S. Macha et al., *Exp. Eye Res.* 2001, 72, 289-99). Following a two hour stabilization, the eyelids of the rabbits were mechanically retracted with Colibri retractors, and a topical well was placed over the eye such that the well was directly on top of the cornea. This positioning allows the drug solution to be in direct contact with the cornea and to exclude the sclera. The outer flange of the topical well was coated with a surgical adhesive to prevent its movement. Subsequent to placing the well, the animals were allowed to stabilize for another 45 minutes to maintain proper intraocular pressure. Following this time period, 150 µl of IPBS containing the radiolabeled compounds [$^{14}$C]-erythromycin (10 µCi/ml), [$^{14}$C]-diazepam (10 µCi/ml), or [$^3$H]-mannitol (10 µCi/ml) were added to the well. The compounds were allowed to diffuse for a period of 75 minutes following which the drug solution was aspirated from the well. The well was subsequently removed, and the corneal surface was washed clean with a few drops of distilled water. Samples were collected every 20 minutes throughout the infusion and post-infusion phases over a period of 7 hours. At the end of the experiment the animals were euthanized under deep anesthesia with an intravenous injection of sodium pentobarbital trough the marginal ear vein. Samples obtained in the study were analyzed by a scintillation counter (LS 6500, Beckman Instruments, Inc., Fullerton, Calif.).

Ocular absorption of erythromycin in the presence of other P-gp substrates was carried out to determine the functionality of P-gp. Dose dependent inhibition of [$^{14}$C]-erythromycin absorption was observed with testosterone. No significant difference was noted in corneal absorption rate ($k_a$) or estimated total drug concentration ($AUC_{0-\infty}$) when testosterone was used at 100 µM or 150 µM. However, a significant inhibition of P-gp efflux (determined by increased absorption) was observed at 250 µM, with the highest inhibition found at 500 µM. At 500 µM of testosterone, a 4-fold increase in $AUC_{0-\infty}$, 5-fold increase in maximum aqueous concentration ($C_{aq,max}$), and a 9-fold increase in the corneal absorption rate were found as compared to control (erythromycin without any testosterone).

Other model P-gp substrates, including cyclosporine A, verapamil, and quinidine were also studied. Cyclosporine A (20 µM) caused a significant increase in $AUC_{0-\infty}$, (2-fold), $k_a$ (3-fold), and $C_{aq,max}$ (2.5-fold) as compared to control. Quinidine (200 µM) also caused inhibition of the P-gp mediated efflux pump. The first order elimination rates ($k_{1O}$) were calculated for all the substrates studied to elucidate if they caused any change in the aqueous elimination pathway. There was no difference observed in the elimination rates for all the substrates as compared to erythromycin alone. The elimination rate constant ($k_{1O}$) ranged from 4.1-5.7 ($\times 10^{-3}$ min$^{-1}$) with elimination half-lives ranging from 122-169 minutes.

EXAMPLE 12

Representative Pharmaceutical Dosage Forms

The following illustrate representative pharmaceutical dosage forms, containing a compound of formula I (Compound X'), for therapeutic or prophylactic use in humans:

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |

| -continued | |
|---|---|
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0-7.5) | q.s. |
| Water for injection | q.s. ad 1 mL |

| (vi) Aerosol | mg/can |
|---|---|
| 'CompoundX' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

| (vii) Ophthalmic Solution or Ointment | mg/ml |
|---|---|
| 'Compound X' | 10-100 |
| Vehicle | |
| Optional Ingredients: | |
| Preservative | 0.01-10 |
| Surfactant | 0.01-10 |
| Chelating agent | 0.01-10 |
| Tonicifier | q.s. to achieve tonicity with lacrimal fluid |
| Buffers | q.s. to maintain pH of formulation within 5.0-7.0 |
| Viscosity agents | q.s. to achieve desired formulation viscosity. |

As used herein, q.s. means quantity sufficient.

If possible the ophthalmic solutions and ophthalmic ointments should be made isotonic with the lacrimal fluids. Preservatives that may be used in the ophthalmic solutions and ointments include quaternary ammonium compounds (e.g., benzalkonium chloride), thimerosal, parabens, and sorbic acid. Chelating agents such as citric acid and preferably disodium EDTA may be used in the ophthalmic solutions and ophthalmic ointments. The chelating agent may also be used to enhance the anti-microbial activity of the primary preservative. Buffers that may be used in the ophthalmic solutions and ophthalmic ointments include acetate, citrate, and borate. Tonicifiers useful in the ophthalmic solutions and ophthalmic ointments include potassium chloride and sodium chloride. Viscosity agents that are useful include the cellulose derivatives, such as hydroxypropylmethyl cellulose. Stabilizing agents, such as antioxidants, e.g., sodium metabisulfite or ascorbic acid, may also be included in the ophthalmic solutions and ophthalmic ointments. The vehicle for an aqueous solution is of course water. For ointments, vehicles can be white petrolatum, anhydrous liquid lanolin, mineral oil, a nonionic lanolin derivative, or another emulsifying agent. It should be understood that various changes can be made in the selection of the above inactives and excipients (e.g., equivalents may be substituted, changes made in materials, etc.) to adapt to a particular formulation objective.

The above formulations may be obtained by conventional procedures well known in the pharmaceutical art.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to incorporate physically into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the statements of the invention. It will be readily apparent to one skilled in the art that varying substitutions and modifications may be made to the invention disclosed herein without departing from the scope and spirit of the invention.

The invention described illustratively herein suitably may be practiced in the absence of any element or elements, or limitation or limitations, which is not specifically disclosed herein as essential. The methods and processes described illustratively herein suitably may be practiced in differing orders of steps, and that they are not necessarily restricted to the orders of steps indicated herein or in the statements of the invention. As used herein and in the appended statements of the invention, the singular forms "a," "an," and "the" include plural reference unless the context clearly dictates otherwise. Thus, for example, a reference to "a pharmaceutical composition" includes a plurality of such compositions, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as set forth in the appended statements of the invention. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended statements of the invention.

The invention has been described broadly and generically herein. Each of the narrower species and subgeneric groupings falling within the generic disclosure also forms part of the invention. This includes the generic description of the invention with a proviso or negative limitation removing any subject matter from the genus, regardless of whether or not the excised material is specifically recited herein.

What is claimed is:

1. A method of delivering a drug to a patient comprising administering to the patient an effective amount of a compound of formula (I):

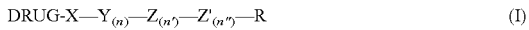

DRUG-X—Y$_{(n)}$—Z$_{(n')}$—Z'$_{(n'')}$—R    (I)

wherein each X, Y, Z, and Z' is independently Met, Val, Thr, Tyr, Trp, Ser, Ala, or Gly; R is H; n is 1, and each n' or n'' is independently 0 or 1; or a pharmaceutically acceptable salt thereof, with the proviso that the compound of formula (I) is influxed into target cells at a rate that is greater than or equal to a rate of influx of the respective DRUG, and is effluxed from target cells into which the compound has previously been influxed at a second rate that is lower than a rate at which the respective DRUG is effluxed from the target cells, wherein DRUG is selected from a set of bioactive compounds consisting of amioderone, lidocaine, quinidine, chloroquine, emetine, hydroxychloroquine, quinacrine, quinine, bepridil, diltiazem, felodipine, nifedipine, nisoldipine, nitrendipine, tiapamil, verapamil, chlorpromazine, trifluperazine, actinomycin D, colchicines, daunorubicin, doxorubicin, etoposide, mitomycin C, mithramycin, puromycin, taxol, topotecan, triamterene, vinblastine, vincristine, indinavir, nelfinavir, ritonavir, saquinavir, aldosterone, clomiphene, cortisol, deoxycorticosterone, progesterone analogs, testosterone, cyclosporine A, cyclosporine H, tacrolimus, sirolimus, reserpine, yohimbine, bupivacaine, desipramine, trazadone, ivermectin, valspodar, and terfindine.

2. The method of claim 1 wherein the compound of formula (I) exhibits an affinity for a nutrient transporter that is greater than the affinity of DRUG for the transporter.

3. The method of claim 2 wherein the nutrient transporter is a peptide transporter.

4. The method of claim 1 wherein each X, Y, Z, and Z' is individually Gly or Val.

5. The method of claim 1 wherein R is H.

6. The method of claim 1 wherein each of n' and n'' is 0.

7. The method of claim 1 wherein —X—Y$_{(n)}$—Z$_{(n')}$—Z$_{(n'')}$—R is a combination of D and L stereoisomeric forms.

8. The method of claim 1 wherein administering is orally administering.

9. The method of claim 1 wherein said DRUG is an antiarrhythmic drug selected from the group consisting of amioderone, lidocaine, and quinidine.

10. The method of claim 1 wherein said DRUG is an antimalarial or antiparasite drug selected from the group consisting of chloroquine, emetine, hydroxychloroquine, quinacrine, and quinine.

11. The method of claim 1 wherein said DRUG is a calcium channel blocker selected from the group consisting of bepridil, diltiazem, felodipine, nifedipine, nisoldipine, nitrendipine, tiapamil, and verapamil.

12. The method of claim 1 wherein said DRUG is a calmodulin antagonist selected from the group consisting of chlorpromazine and trifluperazine.

13. The method of claim 1 wherein said DRUG is a cancer chemotherapeutic selected from the group consisting of actinomycin D, colchicines, daunorubicin, doxorubicin, etoposide, mitomycin C, mithramycin, puromycin, taxol, topotecan, triamterene, vinblastine, and vincristine.

14. The method of claim 1 wherein said DRUG is an HIV protease inhibitor selected from the group consisting of indinavir, nelfinavir, ritonavir, and saquinavir.

15. The method of claim 1 wherein said DRUG is a hormone selected from the group consisting of aldosterone, clomiphene, cortisol, deoxycorticosterone, progesterone analogs, and testosterone.

16. The method of claim 1 wherein said DRUG is an immunosuppressant selected from the group consisting of cyclosporine A, cyclosporine H, tacrolimus, and sirolimus.

17. The method of claim 1 wherein said DRUG is an indole alkaloid selected from the group consisting of reserpine and yohimbin.

18. The method of claim 1 wherein said DRUG is the local anaesthetic bupivacaine.

19. The method of claim 1 wherein said DRUG is a tricyclic antidepressant selected from the group consisting of desipramine and trazadone.

20. The method of claim 1 wherein said DRUG is selected from the group consisting of valspodar and terfindine.

* * * * *